United States Patent
Zamora et al.

(10) Patent No.: US 7,820,172 B1
(45) Date of Patent: Oct. 26, 2010

(54) LAMININ-DERIVED MULTI-DOMAIN PEPTIDES

(75) Inventors: Paul O. Zamora, Gaithersburg, MD (US); Kazuyuki Takahashi, Germantown, MD (US); Xinhua Lin, Plainview, NY (US)

(73) Assignee: BioSurface Engineering Technologies, Inc., Rockville, MD (US)

( * ) Notice: Subject to any disclaimer, the term of this patent is extended or adjusted under 35 U.S.C. 154(b) by 180 days.

(21) Appl. No.: 11/757,242

(22) Filed: Jun. 1, 2007

Related U.S. Application Data

(60) Provisional application No. 60/803,682, filed on Jun. 1, 2006.

(51) Int. Cl.
*A61K 38/04* (2006.01)
*A61K 39/00* (2006.01)

(52) U.S. Cl. .................... 424/185.1; 530/329; 530/325; 530/326; 530/327; 530/328

(58) Field of Classification Search ........................ None
See application file for complete search history.

(56) References Cited

U.S. PATENT DOCUMENTS

| | | |
|---|---|---|
| 3,272,204 A | 9/1966 | Artandi et al. |
| 4,172,128 A | 10/1979 | Thiele et al. |
| 4,193,138 A | 3/1980 | Okita |
| 4,563,350 A | 1/1986 | Nathan et al. |
| 4,747,848 A | 5/1988 | Maini |
| 4,842,575 A | 6/1989 | Hoffman, Jr. et al. |
| 5,108,436 A | 4/1992 | Chu et al. |
| 5,197,977 A | 3/1993 | Hoffman, Jr. et al. |
| 5,509,899 A | 4/1996 | Fan et al. |
| 5,510,418 A | 4/1996 | Rhee et al. |
| 5,563,046 A | 10/1996 | Mascarenhas et al. |
| 5,608,035 A | 3/1997 | Yanofsky et al. |
| 5,635,597 A | 6/1997 | Barrett et al. |
| 5,643,873 A | 7/1997 | Barrett et al. |
| 5,648,458 A | 7/1997 | Cwirla et al. |
| 5,650,234 A | 7/1997 | Dolence et al. |
| 5,654,276 A | 8/1997 | Barrett et al. |
| 5,665,114 A | 9/1997 | Weadock et al. |
| 5,668,110 A | 9/1997 | Barrett et al. |
| 5,674,977 A | 10/1997 | Gariepy |
| 5,679,637 A | 10/1997 | Lappi et al. |
| 5,679,673 A | 10/1997 | Bowen et al. |
| 5,684,136 A | 11/1997 | Godowski |
| 5,728,802 A | 3/1998 | Barrett et al. |
| 5,759,515 A | 6/1998 | Rhodes et al. |
| 5,767,234 A | 6/1998 | Yanofsky et al. |
| 5,770,704 A | 6/1998 | Godowski |
| 5,773,569 A | 6/1998 | Wrighton et al. |
| 5,786,322 A | 7/1998 | Barrett et al. |
| 5,786,331 A | 7/1998 | Barrett et al. |
| 5,789,182 A | 8/1998 | Yayon et al. |
| 5,830,851 A | 11/1998 | Wrighton et al. |
| 5,830,995 A | 11/1998 | Shoyab et al. |
| 5,861,476 A | 1/1999 | Barrett et al. |
| 5,866,113 A | 2/1999 | Hendriks et al. |
| 5,869,451 A | 2/1999 | Dower et al. |
| 5,880,096 A | 3/1999 | Barrett et al. |
| 5,902,799 A | 5/1999 | Herrmann et al. |
| 5,916,585 A | 6/1999 | Cook et al. |
| 5,932,462 A | 8/1999 | Harris et al. |
| 5,945,457 A | 8/1999 | Plate et al. |
| 5,952,474 A | 9/1999 | Kayman et al. |
| 5,955,588 A | 9/1999 | Tsang et al. |
| 5,965,532 A | 10/1999 | Bachovchin |
| 5,989,866 A | 11/1999 | Deisher et al. |
| 5,994,104 A | 11/1999 | Anderson et al. |
| 6,001,364 A | 12/1999 | Rose et al. |
| 6,011,002 A | 1/2000 | Pastan et al. |
| 6,030,812 A | 2/2000 | Bauer et al. |
| 6,051,648 A | 4/2000 | Rhee et al. |
| 6,096,798 A | 8/2000 | Luthra et al. |
| 6,099,562 A | 8/2000 | Ding et al. |
| 6,120,904 A | 9/2000 | Hostettler et al. |
| 6,121,236 A | 9/2000 | Ben-Sasson |
| 6,168,784 B1 | 1/2001 | Offord et al. |

(Continued)

FOREIGN PATENT DOCUMENTS

WO WO-WO00/18921 4/2000

(Continued)

OTHER PUBLICATIONS

Healy et al. Designing biomaterials to direct biological responses. Ann N Y Acad Sci. Jun. 18, 1999;875:24-35.*

(Continued)

*Primary Examiner*—Maher M Haddad
(74) *Attorney, Agent, or Firm*—Janeen Vilven; Peacock Myers, P.C.

(57) ABSTRACT

Multi-domain peptides including a heparin-binding peptide sequence covalently linked to a linker sequence, which linker sequence is covalently linked to a trifunctional amino acid residue forming a branch with two arms, with substantially similar (homodimeric) cellular attachment peptide sequences covalently linked, directly or through an intermediate, to each branch arm, where the sequences are cell binding analogs of or derived from laminin or a portion of laminin. Further provided are preparations for medical devices, pharmaceutical compositions and methods of using the same.

6 Claims, 5 Drawing Sheets

U.S. PATENT DOCUMENTS

| | | |
|---|---|---|
| 6,174,530 B1 | 1/2001 | Rose et al. |
| 6,174,721 B1 | 1/2001 | Innis et al. |
| 6,214,795 B1 | 4/2001 | Benjamin et al. |
| 6,217,873 B1 | 4/2001 | Rose et al. |
| 6,231,600 B1 | 5/2001 | Zhong |
| 6,231,892 B1 | 5/2001 | Hubbell et al. |
| 6,235,716 B1 | 5/2001 | Ben-Sasson |
| 6,248,057 B1 | 6/2001 | Mavity et al. |
| 6,251,864 B1 | 6/2001 | Dower et al. |
| 6,258,371 B1 | 7/2001 | Koulik et al. |
| 6,270,788 B1 | 8/2001 | Koulik et al. |
| 6,284,503 B1 | 9/2001 | Caldwell et al. |
| 6,294,359 B1 | 9/2001 | Fiddes et al. |
| 6,306,165 B1 | 10/2001 | Patnaik et al. |
| 6,309,660 B1 | 10/2001 | Hsu et al. |
| 6,323,323 B1 | 11/2001 | Sledziewski et al. |
| 6,326,468 B1 | 12/2001 | Canne et al. |
| 6,342,591 B1 | 1/2002 | Zamora et al. |
| 6,350,731 B1 | 2/2002 | Jehanli et al. |
| 6,368,347 B1 | 4/2002 | Maini et al. |
| 6,377,349 B1 | 4/2002 | Fercher |
| 6,387,978 B2 | 5/2002 | Ronan et al. |
| 6,406,687 B1 | 6/2002 | Luthra et al. |
| 6,410,044 B1 | 6/2002 | Chudzik et al. |
| 6,426,332 B1 | 7/2002 | Rueger et al. |
| 6,451,543 B1 | 9/2002 | Kochendoerfer et al. |
| 6,458,889 B1 | 10/2002 | Trollsas et al. |
| 6,491,965 B1 | 12/2002 | Berry et al. |
| 6,497,729 B1 | 12/2002 | Moussy et al. |
| 6,514,534 B1 | 2/2003 | Sawhney |
| 6,534,591 B2 | 3/2003 | Rhee et al. |
| 6,548,634 B1 | 4/2003 | Ballinger et al. |
| 6,585,765 B1 | 7/2003 | Hossainy et al. |
| 6,596,699 B2 | 7/2003 | Zamora et al. |
| 6,630,580 B2 | 10/2003 | Tsang et al. |
| 6,818,018 B1 | 11/2004 | Sawhney |
| 6,846,853 B2 | 1/2005 | Shimp |
| 6,863,899 B2 | 3/2005 | Koblish et al. |
| 6,921,811 B2 | 7/2005 | Zamora et al. |
| 6,949,251 B2 | 9/2005 | Dalal et al. |
| 6,984,393 B2 | 1/2006 | Amsden |
| 7,025,990 B2 | 4/2006 | Sawhney |
| 7,041,641 B2 | 5/2006 | Rueger et al. |
| 7,166,574 B2 | 1/2007 | Pena et al. |
| 7,241,736 B2 | 7/2007 | Hunter et al. |
| 7,414,028 B1 | 8/2008 | Zamora et al. |
| 7,468,210 B1 | 12/2008 | Zamora |
| 7,482,427 B2 | 1/2009 | Pena et al. |
| 7,528,105 B1 | 5/2009 | Pena et al. |
| 7,598,224 B2 | 10/2009 | Zamora et al. |
| 2001/0014662 A1 | 8/2001 | Rueger et al. |
| 2002/0115836 A1 | 8/2002 | Tsang et al. |
| 2002/0160098 A1 | 10/2002 | Zamora et al. |
| 2003/0224996 A1 | 12/2003 | Opperman et al. |
| 2004/0038348 A1 | 2/2004 | Pena et al. |
| 2004/0068266 A1 | 4/2004 | Delmotte |
| 2004/0087505 A1* | 5/2004 | Pena et al. .................... 514/12 |
| 2004/0151764 A1 | 8/2004 | Zamora |
| 2005/0196425 A1 | 9/2005 | Zamora |
| 2005/0222394 A1 | 10/2005 | Zamora et al. |
| 2006/0024347 A1 | 2/2006 | Zamora et al. |
| 2006/0199764 A1 | 9/2006 | Zamora et al. |
| 2006/0205652 A1 | 9/2006 | Zamora et al. |
| 2008/0063622 A1 | 3/2008 | Zamora et al. |
| 2008/0160169 A1 | 7/2008 | Zamora et al. |
| 2008/0166392 A1* | 7/2008 | Zamora et al. .............. 424/426 |
| 2008/0227696 A1* | 9/2008 | Takahashi et al. ............. 514/12 |
| 2009/0111743 A1 | 4/2009 | Takahashi |
| 2009/0143566 A1 | 6/2009 | Zamora et al. |

FOREIGN PATENT DOCUMENTS

| | | |
|---|---|---|
| WO | WO-WO00/64481 | 11/2000 |
| WO | WO-WO02/04015 | 1/2002 |
| WO | WO-WO02/10221 | 2/2002 |
| WO | WO-WO02/19963 | 3/2002 |
| WO | WO-WO02/20033 | 3/2002 |
| WO | WO-02/062823 | 8/2002 |

OTHER PUBLICATIONS

Tong et al. Peptide surface modification of poly(tetrafluoroethylene-co-hexafluoropropylene) enhances its interaction with central nervous system neurons. J Biomed Mater Res, 42, 85-95, 1998.*

Lu X et al Preferential antagonism of the interactions of the integrin alpha IIb beta 3 with immobilized glycoprotein ligands by snake-venom RGD (Arg-Gly-Asp) proteins. Evidence supporting a functional role for the amino acid residues flanking the tripeptide RGD in determining the inhibitory properties of snake-venom ..(1994) Biochem J 304: 929-936.*

Yano et al. RGD motif enhances immunogenicity and adjuvanicity of peptide antigens following intranasal immunization. Vaccine. Dec. 12, 2003;22(2):237-43.*

Ahmed, Asif et al., "Role of VEFGF Receptor-1 (Fit-1) in Mediating Calcium-Dependent Nitric Oxide Release and Limiting DNA Synthesis in Human Trophoblast Cells", *Lab Invest.*, vol. 76(6) Jun. 1977, 779-791.

Andrades, Jose A. et al., "A Recombinant Human TGF-B1 Fusion Protein with Collagen-Binding Domain Promostes Migration, Growth, and Differentiation of Bone Marrow Mesenchymal Cells", *Experimental Cell Research* vol. 250 1999, 485-498.

Baird, Andrew et al., "Receptor- and heparin-binding domains of basic fibroblast growth factor", *Proc. Natl. Acad. Sci.*, vol. 85 Apr. 1988, 2324-2328.

Ballinger, Marcus D. et al., "Semirational design of a potent, artificial agonist of fibroblast growth factor receptors", *Nature Biotechnology* vol. 17 1999, 1199-1204.

Binetruy-Tournaire, Roselyne et al., "Identification of a Peptide Blocking Vascular Endothelial Growth Factor (VEGF)-mediated Angiogenesis", *The EMBO Journal*, vol. 19, No. 7 2000, 1525-1533.

Bork, Peer, "Go Hunting in Sequence Databases But Watch Out For Traps", *TIG* Vo. 12 No. 10 Oct. 1996, 425-427.

Bork, Peer, "Powers and Pitfalls In Sequence Analysis: the 70% Hurdle", *Genome Research* vol. 10 2000, 398-400.

Brennand, David M. et al., "Identification of a Cyclic Peptide Inhibitor of Platelet-Derived Growth Factor-BB Receptor-Binding and Mitogen-Induced DNA Synthesis in Human Fibroblasts", *FEBS Letters*, 413 1997, 70-74.

Brenner, Steve, "Errors in Genome Annotation", *Trends in Genetics* vol. 15 No. 4 Apr. 1999, 132-133.

Carmeliet, Peter et al., "Growing Better Blood Vessels", *Nature Biotechnology* vol. 19 2001, 1019-1020.

Dawson, Philip E. et al., "Synthesis of Native Proteins by Chemical Ligation", *Annu. Rev. Biochem*, 2000, 69, 923-960.

Dikov, Michael M. et al., "A Functional Fibroblast Growth Factor-1 Immunoglogulin Fusion Protein", *The Journal of Biological Chemistry*, vol. 273, No. 25 Jun. 19, 1998, 15811-15817.

Doerks, Tobias, "Protein annotation: detective work for function prediction", *Trends in Genetics* vol. 14 No. 6 Jun. 1998, 248-250.

Engstrom, Ulla et al., "Identification of a Peptide Antagonist for Platelet-Derived Growth Factor", *The Journal of Biological Chemistry*, vol. 273, No. 25 1998, 16581-16587.

Eom, Khee D. et al., "Tandem Ligation of Multipartite Peptides with Cell-Permeable Activity", *J. Am. Chem. Soc.* vol. 125 2003, 73-83.

Feeley, Brian et al., "Influence of BMP's on the Formation of Osteoblastic Lesions in Metastatic Prostate Cancer", *Journal of Bone and Mineral Research*, vol. 20 No. 12 2005, 2189-2199.

Gay, Cyril G. et al., "Interleukin 1 regulated heparin-binding growth factor 2 gene expression in vascular smooth muscle cells", *Proc. Natl. Acad. Sci. USA*, vol. 88 Jan. 1991, 296-300.

Hasan, Maemunah et al., "IL-12 is a Heparin-Binding Cytokine", *The Journal of Immunology* vol. 162 1999, 1064-1070.

Hoke, David E. et al., "A Heparin Binding Synthetic Peptide from Human HIP/RPL29 Fails to Specifically Differentiate Between Anticoagulantly Active and Inactive Species of Heparin", *Journal of Negative Results in BioMedicine* vol. 2. No. 1 2003, 1-10.

Kirsch, Thomas et al., "BMP-2 Antagonists Emerge from Alterations in the Low-Affinity Binding Epitope for Receptor BMPR-II", *EMBO Journal*, vol. 19, No. 13 2000, 3314-3324.

Kloen, P. et al., "BMP signaling components are expressed in human fracture callus", *Bone* 33 2003, 362-371.

Kochendoerfer, Gerd G. et al., "Design and Chemical Synthesis of Homogeneous Polymer-Modified Erythropoiesis Protein", *Science*, vol. 299 2003, 884-887.

Konishi, Sadahiko et al., "Hydroxyapatite Granule Graft Combined with Recombinant Human bone Morphogenic Protein-2 for Solid Lumbar Fusion", *Journal of Spinal Disorders & Techniques*, vol. 15, No. 3 2002, 237-244.

Laredo, James et al., "Silyl-heparin bonding improves the patency and in vivo thromboresistance of carbon-coated polytetrafluoroethylene vascular grafts", *The Midwestern Vascular Surgical Society* Sep. 2003, 1-7.

Lin, Xinhua et al., "A Synthetic, Bioactive Pdgf Mimetic with Binding to Both α-PDGF and β-PDGF Receptors", *Growth Factors* vol. 25 No. 2 2007, 87-93.

Minamide, Akihito et al., "Evaluation of Carriers of Bone Morphogenetic Protein for Spinal Fusion", *Spine* vol. 26, No. 8 2001, 933-939.

Murnaghan, Mark et al., "Time for treating bone fracture using rhBMP-2: A randomised placebo controlled mouse fracture trial", *Journal of Orthopaedic Research* 23 2005, 625-631.

Ngo, Thomas et al., "Computational Complexity; Protein Structure Prediction, and the Levinthal Paradox", *The Protein Foling Problem and Terminary Structure Prediction*, Chapter 14 1994, 491-495.

Niikura, T. et al., "Gloval Gene Profiling in Experimental Fracture Nonunions Reveals a Down Regulation of BMP Gene Expression", *52nd Annual Meeting of the Orthopaedic Research Society* Paper No. 1673 2006.

Ostman, Arne et al., "Identification of Three Amino Acids in the Platelet-Derived Growth Factor (PDGF) B-chain that are Important for Binding to the PDGF B-Receptor", *The Journal of Biological Chemistry*, vol. 266, No. 16, Issue of Jun. 5 1991, 10073-10077.

Paris, Francois et al., "Endothelial Apoptosis as the Primary Lesion Initiating Intestinal Radiation Damage in Mice", *Science* vol. 293 2001, 293-297.

Pellegrini, Luca, "Role of Heparan sulfate in fibroblast growth factor signalling: a structural view", *Current Opinion in Structural Biology* 2001, 629-634.

Ray, Jasohara et al., "A 10-amino acid sequence of fibroblast growth factor 2 is sufficient for its mitogenic activity on neural progenitor cells", *Proc. Natl. Acad. Sci. USA* vol. 94 1997, 7047-7052.

Richardson, Thomas P. et al., "Polymeric system for dual growth factor delivery", *Nature Biotechnology* vol. 19 2001, 293-297.

Rusnati, Marco et al., "avB3 Integrin Mediates the Cell-adhesive Capacity and Biological Activity of Basic Fibroblast Growth Factor (FGF-2) in Cultured Endothelial Cells", *Molecular Biology of the Cell* vol. 8 1997, 2449-2461.

Saito, Atsuhiro et al., "Activation of osteo-progenitor cells by a novel synthetic peptide derived from the bone morphogenetic protein-2 knuckle epitope", *Biochimica et Biophysica Acta* 1651 2003, 60-67.

Saito, Atsuhiro et al., "Prolonged ectopic calcification induced by BMP-2-derived synthetic peptide", *Journal of Biomedical Materials Research Part A*, vol. 70 No. 1 2004, 115-121.

Seol, Yang-Jo et al., "Enhanced osteogenic promotion around dental implants with synthetic binding motif mimicking bone morphogenetic protein (BMP)-2", *Journal of Biomedical Materials Research Part A*, vol. 77 No. 3 2006, 599-607.

Shen, Wei-Chiang et al., "Poly(l-lysine) has different membrane transport and drug-carrier properties when complexed with heparin", *Proc Natl Acad Sci USA* vol. 78, No. 12 Dec. 1981, 7589-93.

Skolnick, Jeffrey et al., "From genes to protein structure and function: novel applications of computational approaches in the genomic era", *TIBTECH* vol. 18 Jan. 2000, 34-39.

Smith, Temple F. et al., "The challenges of genome sequence annotation of "The devil is in the details"", *Nature Biotechnology*, vol. 15 Nov. 1997, 1222-1223.

Sood, R. et al., "MDS1/EVI1 enhances TGF-B1 signaling and strengthens its growth-inhibitory effect, but the leukemia-associated fusion protein AML1/MDS1/EVI1, product of the t(3:21), abrogates growth-inhibition in response to TGF-B1", *Leukemia* vol. 13 1999, 348-357.

Takizawa, Takuma et al., "Directly Linked Soluble IL-6 Receptor-IL-6 Fusion Protein Induces Astrocyte Differentiation from Neuroepithelial Cells Via Activation of STAT3", *Cytokine* vol. 13 2001, 272-279.

Tanaka, H. et al., "Involvement of bone morphogenic protein-2 (BMP-2) in the pathological ossification process of the spinal ligament", *Rheumatology* 2001;40 May 9, 2001, 1163-1168.

Tung, Ching-Hsuan et al., "Novel branching membrane translocational peptide as gene delivery vector", *Bioorg Med Chem* 10(11) 2002, 3609-3614.

Varkey, Mathew et al., "Growth factor delivery for bone tissue repair: an update", *Expert Opin. Drug Deliver.* (2004) 1(1) 2004, 19-34.

Verrecchio, Angela, "Design of Peptides with High Affinities for Heparin and Endothelial Cell Proteoglycans", *The Journal of Biological Chemistry*, vol. 275, No. 11 Mar. 17, 2000, 7701-7707.

Wells, James A., "Additivity of Mutational Effects in Proteins", *American Chemical Society*, vol. 29, No. 37 Sep. 18, 1990, 8509-8516.

Yoneda, Atsuko, "Engineering of an FGF-proteoglycan fusion protein with heparin-independent, mitogenic activity", *Nature Biotechnology* vol. 18 Jun. 2000, 641-644.

Zamora, Paul O. et al., "Local Delivery of Basic Fibroblast Growth Factor (bFGF) Using Adsorbed Silyl-heparin, Benzyl-bis(dimethylsilylmethyl)oxycarbamoyl-heparin", *Bioconjugate Chem.* 2002 Aug. 20, 2002, 920-926.

\* cited by examiner

LAMININ-DERIVED MULTI-DOMAIN PEPTIDES

INTRODUCTION

The invention relates to the field of synthetic peptides and analogs of laminin-derived peptides, including homodimeric synthetic laminin-derived analogs wherein two sequences are branched from a single branch point, the single branch point including at least one trifunctional amino acid residue, which branch point is further covalently bonded to a heparin-binding sequence, directly or through a hydrophobic linker sequence. The invention further relates to the clinical uses of such multi-domain peptides as soluble drugs and as coatings for medical devices.

BACKGROUND OF THE INVENTION

Note that the following discussion refers to a number of publications by author(s) and year of publication. Discussion of such publications herein is given for more complete background and is not to be construed as an admission that such publications are prior art for patentability determination purposes.

Surface modification of medical implants is frequently desired to increase cell adhesion and tissue integration into the implant. Increasing cell adhesion is of particular interest with polytetrafluoroethylene (ePTFE) prostheses but is also of interest in implants of other materials, such as titanium which is frequently used in orthopedic applications. (See for example Bellon et al. Similarity in behavior of polytetrafluoroethylene (ePTFE) prostheses implanted into different interfaces. J Biomed Mater Res 31 (1996) 1-9; Bagno and Di Bello, Surface treatments and roughness properties of Ti-based biomaterials. J Mater Sci Mater Med 15 (2004) 935-49; and Goto et al. The initial attachment and subsequent behavior of osteoblastic cells and oral epithelial cells on titanium. Biomed Mater Eng 14 (2004) 537-44).

One approach to increasing cell adhesion is the use of bioactive cell adhesion peptides motifs found in extracellular matrix molecules such as collagens, fibronectin, and laminin, among others. As an example, P-15, a collagen-derived peptide, increases cell attachment and modulates a number of gene products, and has been incorporated into a commercially-available dental implant. (See for example Bhatnagar et al. Design of biomimetic habitats for tissue engineering with P-15, a synthetic peptide analogue of collagen., Tissue Eng 5 (1999) 53-65; Carinci et al. P-15 cell-binding domain derived from collagen: analysis of MG63 osteoblastic-cell response by means of a microarray technology. J Periodontol 75 (2004) 66-83; and Lucidarme, et al. Angiogenesis model for ultrasound contrast research: exploratory study, Acad Radiol 11 (2004) 4-12).

Other peptides with cell binding motifs that have been investigated for use on implants include those based on RGD, YIGSR (SEQ ID NO:1) and IKVAV (SEQ ID NO:2) motifs derived from laminin. Heparin-binding peptides including those from laminin can also directly promote cell adhesion and may also be similarly used. (See for example Shin et al. Biomimetic materials for tissue engineering. Biomaterials 24 (2003) 4353-64; Skubitz et al. Synthetic peptides from the carboxy-terminal globular domain of the A chain of laminin: their ability to promote cell adhesion and neurite outgrowth, and interact with heparin and the beta 1 integrin subunit. J Cell Biol 115 (1991) 1137-48; Yokoyama et al. Cyclic peptides from the loop region of the laminin alpha 4 chain LG4 module show enhanced biological activity over linear peptides. Biochemistry 43 (2004) 13590-7; and Yoshida et al. Identification of a heparin binding site and the biological activities of the laminin alpha1 chain carboxy-terminal globular domain. J Cell Physiol 179 (1999) 18-28).

Also known are constructs called heterogeneous mimetic peptide surfaces (MPS) containing both RGD (cell-binding) and FHRRIKA (SEQ ID NO:18) (putative heparin-binding) sequences, which are reported to enhance cell attachment and differentiation. (See for example Healy et al. Designing biomaterials to direct biological responses. Ann N Y Acad Sci 875 (1999) 24-35).

Laminins are large glycoproteins (molecular mass≈900 kDa) found in basement membranes where they are major components. (See for example Colognato and Yurchenco. Form and function: the laminin family of heterotrimers. Dev Dyn 218 (2000) 213-34). Laminin-1 consists of three chains designated a1 (400 kDa), b1 (210 kDa) and c1 (200 kDa), which are arranged in a cross-shaped structure, and contribute to cell differentiation, cell shape and movement, maintenance of tissue phenotypes, and promotion of tissue survival. Laminin binds heparin as do laminin-derived peptides such as KEGYKVRLDLNITLEFRTTSK (SEQ ID NO:3) and KATPMLKMRTSFHGCIK (SEQ ID NO:4); IKLLI (SEQ ID NO:5), and KDFLSIELVRGRVK (SEQ ID NO:6). (See for example Edgar and Thoenen. The heparin-binding domain of laminin is responsible for its effects on neurite outgrowth and neuronal survival. Embo J 3 (1984) 1463-8; Skubitz, et al. Synthetic peptides from the carboxy-terminal globular domain of the A chain of laminin: their ability to promote cell adhesion and neurite outgrowth, and interact with heparin and the beta 1 integrin subunit. J Cell Biol 115 (1991) 1137-48; Tashiro et al. An IKLLI-containing peptide derived from the laminin alpha1 chain mediating heparin-binding, cell adhesion, neurite outgrowth and proliferation, represents a binding site for integrin alpha3beta1 and heparan sulphate proteoglycan. Biochem J 340 (Pt 1) (1999) 119-26; Yoshida et al. Identification of a heparin binding site and the biological activities of the laminin alpha1 chain carboxy-terminal globular domain. J Cell Physiol 179 (1999) 18-28).

Those peptides also affect cell adhesion. Laminin also contains numerous other cell-adhesion sites in its α, β, and γ chains including RGD LGTIPG (SEQ ID NO:7), YIGSR (SEQ ID NO:1), RYVVLPR (SEQ ID NO:8), PDSGR (SEQ ID NO:9), YFQRYLI (SEQ ID NO:10), LRE, IKLLI (SEQ ID NO:11), RNIAEIIKDI (SEQ ID NO:12), SIYITRF (SEQ ID NO:13), IARQRN (SEQ ID NO:14), LQVQLSIR (SEQ ID NO:15), IKVAV (SEQ ID NO:2), and several others in the globular domain (GD) of the α chain. At the cell surface, RGD and KQNCLSSRASFRGCVRNLRLSR (SEQ ID NO:17) (the GD-6 peptide) bind to integrins; YIGSR (SEQ ID NO:1) and LGTIPG (SEQ ID NO:7) bind to a 67 kDa protein; and IKVAV (SEQ ID NO:2) to a 110 kDa protein.

The central role of laminins in cell attachment has, in part, lead to studies using laminin to improve cell attachment to implants, including vascular grafts, neural implants, and dental implants. (See for example J. W. Dean, 3rd et al. Fibronectin and laminin enhance gingival cell attachment to dental implant surfaces in vitro. Int J Oral Maxillofac Implants 10 (1995) 721-8; Healy et al. Designing biomaterials to direct biological responses. Ann N Y Acad Sci 875 (1999) 24-35; Huber et al. Modification of glassy carbon surfaces with synthetic laminin-derived peptides for nerve cell attachment and neurite growth. J Biomed Mater Res 41 (1998) 278-88; Kidd et al. Stimulated endothelial cell adhesion and angiogenesis with laminin-5 modification of expanded polytetrafluoroethylene. Tissue Eng 11 (2005) 1379-91; Kidd and Williams. Laminin-5-enriched extracellular matrix accelerates angiogenesis and neovascularization in association with ePTFE. J Biomed Mater Res A 69 (2004) 294-304; Massia et al. In vitro assessment of bioactive coatings for neural implant applications. J Biomed Mater Res A 68 (2004) 177-86; Tamura et al. Coating of titanium alloy with soluble laminin-5 promotes cell attachment and hemidesmosome assembly in gingival epithelial cells: potential application to dental implants. J Periodontal Res 32 (1997) 287-94).

While recombinant laminins have been made, a synthetic peptide based on laminin may provide significant advantages for use on medical devices. (See for example Kortesmaa et al. Recombinant laminin-8 (alpha(4)beta(1)gamma(1)). Production, purification, and interactions with integrins. J Biol Chem 275 (2000) 14853-9; Mathus and Yurchenco. Analysis of laminin structure and function with recombinant glycoprotein expressed in insect cells. Methods Mol Biol 139 (2000) 27-37; Sung et al. Localization of heparin binding activity in recombinant laminin G domain. Eur J Biochem 250 (1997) 138-43; Yurchenco et al. Recombinant laminin G domain mediates myoblast adhesion and heparin binding. J Biol Chem 268 (1993) 8356-65).

IKVAV (SEQ ID NO:2) promotes cell adhesion and differentiation of several different cell types. With endothelial cells for example, IKVAV (SEQ ID NO:2) induces tube formation, aortic spouting, angiogenesis, and mediates revascularization of ischemic tissue. (See for example Huber et al. Modification of glassy carbon surfaces with synthetic laminin-derived peptides for nerve cell attachment and neurite growth. J Biomed Mater Res 41 (1998) 278-88., Grant et al. Interaction of endothelial cells with a laminin A chain peptide (SIKVAV) in vitro and induction of angiogenic behavior in vivo. J Cell Physiol 153 (1992) 614-25; Grant and Zukowska. Revascularization of ischemic tissues with SIKVAV and neuropeptide Y (NPY), Adv Exp Med Biol 476 (2000) 139-54; Malindary et al. Ponce, Identification of laminin alpha1 and beta1 chain peptides active for endothelial cell adhesion, tube formation, and aortic sprouting, Faseb J 13 (1999) 53-62). With nerve cells, IKVAV (SEQ ID NO:2) also mediates cell attachment and growth and has been used in the construction of experimental nerve guides. (See for example Massia et al. In vitro assessment of bioactive coatings for neural implant applications. J Biomed Mater Res A 68 (2004) 177-86; D. Shaw and M. S. Shoichet. Toward spinal cord injury repair strategies: peptide surface modification of expanded poly(tetrafluoroethylene) fibers for guided neurite outgrowth in vitro. J Craniofac Surg 14 (2003) 308-16; Tong and Shoicliet. Enhancing the neuronal interaction on fluoropolymer surfaces with mixed peptides or spacer group linkers. Biomaterials 22 (2001) 1029-34).

Laminin-derived constructs described as peptide amphiphiles are known, which constructs incorporate a hydrophobic component. Linear constructs are described in U.S. Patent Application 2005/0214257, published Sep. 29, 2005, and non-linear constructs are described in U.S. Patent Application 2005/0208589, published Sep. 22, 2005. However, none of these constructs include a heparin-binding component. Additionally, these constructs are described primarily as useful for stem cell regulation, enhancing epitope presentation and similar indications.

There is thus a need for cost-effective synthetic peptide constructs that promote cellular attachment, and are useful for coating medical devices and as soluble biologics, and as pharmaceutical agents for treating a variety of conditions.

SUMMARY OF THE INVENTION

The invention provides a multi-domain peptide, comprising a heparin-binding sequence covalently linked to a linker sequence, which linker sequence is covalently linked to a trifunctional amino acid residue forming a branch with two arms, with a cellular attachment peptide sequence covalently linked, directly or through an intermediate, to each branch arm. In the multi-domain peptide, preferably the cellular attachment peptide sequence is not a heparin-binding growth factor or derivative of a heparin-binding growth factor. Preferably in the multi-domain peptide the cellular attachment peptide sequence is derived from laminin. Where the cellular attachment peptide sequence is derived from laminin, it may include KEGYKVRLDLNITLEFRTTSK (SEQ ID NO:3), KATPMLKMRTSFHGCIK (SEQ ID NO:4), IKLLI (SEQ ID NO:5), KDFLSIELVRGRVK (SEQ ID NO:6), RGD, LGTIPG (SEQ ID NO:7), YIGSR (SEQ ID NO:1), RYVV-LPR (SEQ ID NO:8), PDSGR (SEQ ID NO:9), YFQRYLI (SEQ ID NO:10), LRE, IKLLI (SEQ ID NO:11), RNIAEI-IKDI (SEQ ID NO:12), SIYITRF (SEQ ID NO:13), IAR-QRN (SEQ ID NO:14), LQVQLSIR (SEQ ID NO:15), IKVAV (SEQ ID NO:2), or KQNCLSSRASFRGCVRNL-RLSR (SEQ ID NO:17). In one aspect, the cellular attachment peptide sequence includes IKVAV (SEQ ID NO:2).

The multi-domain peptide of the invention may be of formula I:

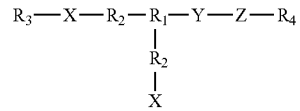

where each X is the cellular attachment peptide sequence; $R_1$ is the single trifunctional amino acid residue; each $R_2$ is the same or different and comprises from 0 to about 5 amino acid residues covalently bonded to $R_1$ and X; each $R_3$ is hydrogen (H) such that the terminal group is $NH_2$, or is an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or is from one to about three amino acid residues with a terminal H, such that the terminal group is $NH_2$, or an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative; $R_4$ is OH such that the terminal group is a carboxyl, $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or NH—$R_3$; Y is the linker sequence covalently bonded to $R_1$ and Z; and Z is the heparin-binding sequence.

In one aspect of the multi-domain peptide of formula I, each $R_3$ is H—S—, where H is hydrogen; each X is YIGSR (SEQ ID NO:2); each $R_2$ is -AA-; $R_1$ is K; Y is -Ahx-Ahx-Ahx-; Z is RKRKLERIAR (SEQ ID NO: 20); and $R_4$ is —$NH_2$, where N is nitrogen and H is hydrogen.

In one aspect of the multi-domain peptide of formula I, $R_1$ is an L- or D-diamine amino acid residue selected from the group consisting of 2,3 diamino propionyl amino acid, 2,4 diamino butylic amino acid, lysine and ornithine. $R_2$ may be from 1 to about 5 L- or D-amino acid residues selected from the group consisting of glycine, alanine, leucine and combinations of the foregoing.

In another aspect, the multi-domain peptide of formula I may be characterized in that it has an avidity for heparin such that the multi-domain peptide binds heparin in 0.15 M NaCl, but is eluted by greater than about 0.5 M NaCl.

In yet another aspect, there is provided a multi-domain peptide of formula II:

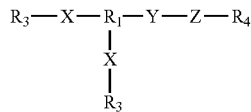

wherein $R_1$ is a diamine amino acid.

In yet another aspect, there is provided a multi-domain peptide of formula III:

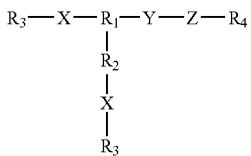

where $R_1$ is a trifunctional amino acid wherein the side chain of $R_1$ comprises a reactive sulfhydryl; and $R_2$ comprises a trifunctional amino acid wherein the side chain comprises a reactive sulfhydryl, wherein $R_2$ is covalently bonded to $R_1$ by a disulfide bond. In the multi-domain peptide of formula III, $R_1$ and $R_2$ can each independently be an L- or D-3-mercapto amino acid selected from the group consisting of L- or D-cysteine, L- or D-penicillamine, 3-mercapto phenylalanine, and a derivative of any of the foregoing.

In yet another aspect, there is provided a multi-domain peptide of formula IV:

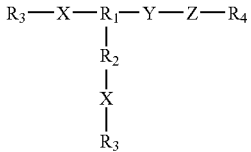

where $R_1$ is a trifunctional amino acid wherein the side chain comprises a first reactive group; and $R_2$ comprises a trifunctional amino acid wherein the side chain comprises a second reactive group, wherein $R_2$ is covalently bonded to $R_1$ by a covalent bond between the first reactive group and the second reactive group.

In yet another aspect there is provided rte multi-domain peptide of formula V:

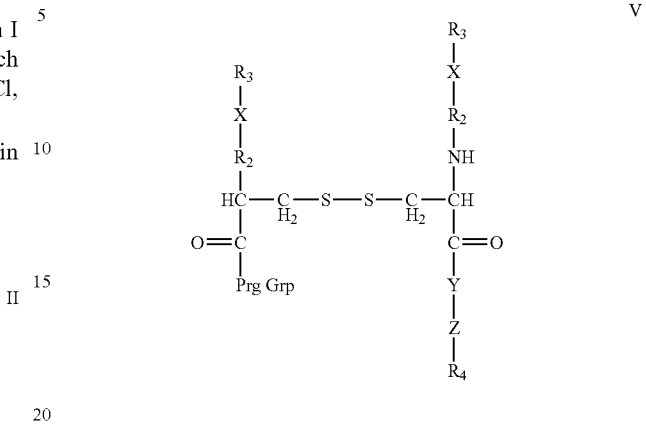

where Prg Grp is OH or a carboxy terminus protecting group; and C is carbon, H is hydrogen, N is nitrogen, O is oxygen and S is sulfur. In one aspect of the multi-domain peptide of formula V, each $R_2$ is not present, each $R_3$ is H and $R_4$ is $-NH_2$.

In another aspect, the invention provides a multi-domain peptide comprising two sequences branched from a single residue, the two sequences being the same and comprising a cellular attachment peptide sequence, and a sequence comprising a heparin-binding sequence covalently bonded directly or through a linker sequence to the single residue. The heparin-binding sequence may be covalently bonded to the single residue by means of a linker, which linker may be hydrophobic. The single residue is in one embodiment a trifunctional amino acid residue.

In any of the foregoing multi-domain peptides, in one aspect the linker sequence comprises $[NH_2-(CH_2)_pCO]_q$ wherein p is from 1 to about 10 and q is from 1 to about 20. In another aspect, the linker sequence comprises between one and about thirty-three ethylene glycol units. In another aspect the linker sequence comprises a branched or unbranched, saturated or unsaturated alkyl chain of between one and about twenty carbon atoms. In yet another aspect the linker sequence comprises from 1 to about 5 L- or D-amino acid residues selected from the group consisting of glycine, alanine, leucine and combinations of the foregoing.

In any of the foregoing multi-domain peptides, in one aspect the heparin binding sequence comprises BxBB (SEQ ID NO:27) or BBBxxB (SEQ ID NO:28), wherein each B is independently lysine, arginine, ornithine, or histidine, and each x is a independently a naturally occurring amino acid. In another aspect the heparin binding sequence comprises more than one of BxBB or BBBxxB, wherein each B is independently lysine, arginine, ornithine, or histidine, and each x is a independently a naturally occurring amino acid. In yet another aspect the heparin binding sequence comprises RKRKLERIAR (SEQ ID NO: 20), RKRKLGRIAR (SEQ ID NO:21), RKRKLWRARA (SEQ ID NO:22), RKRLDRIAR (SEQ ID NO:23) or RKRKLERIARC (SEQ ID NO:24).

In any of the foregoing multi-domain peptides, in one aspect the covalent bonds between $R_1$ and Y comprise an amide, disulfide, thioether, Schiff base, reduced Schiff base, imide, secondary amine, carbonyl, urea, hydrazone or oxime bond. In another aspect the covalent bonds between $R_1$ and each X comprise an amide, disulfide, thioether, Schiff base, reduced Schiff base, imide, secondary amine, carbonyl, urea, hydrazone or oxime bond. In yet another aspect the covalent bonds between Y and Z comprise an amide, disulfide, thioether, Schiff base, reduced Schiff base, imide, secondary amine, carbonyl, urea, hydrazone or oxime bond.

In one embodiment the invention provides a pharmaceutical composition comprising the multi-domain peptide as described above or a pharmaceutically acceptable salt thereof and a pharmaceutical carrier. In another embodiment, the invention provides a medical device comprising at least one tissue contacting surface coated with a multi-domain peptide as described above or a pharmaceutically acceptable salt thereof.

In one preferred embodiment, the invention provides a multi-domain peptide of the formula H-SIKVAVAAK(H-SIKVAVAA)-Ahx-Ahx-Ahx-RKRKLERIAR-NH$_2$, hereafter "MD Peptide 1", where H is hydrogen, Ahx is aminohexanoic acid, NH$_2$ is an amino group, and the remaining letters are single letter codes for amino acid residues.

The present invention also provides a method for delivering an active peptide to a mammal, particularly a human. The method includes providing a medical device coated on the surface thereof via non-covalent bonds with a multi-domain peptide of any of formulas I to V and placing the medical device onto a surface of, or implanting the medical device into, the mammal.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

Additional objects and advantages of the present invention will be apparent in the following detailed description read in conjunction with the accompanying drawing figures.

DETAILED DESCRIPTION OF THE INVENTION

Figure 1:
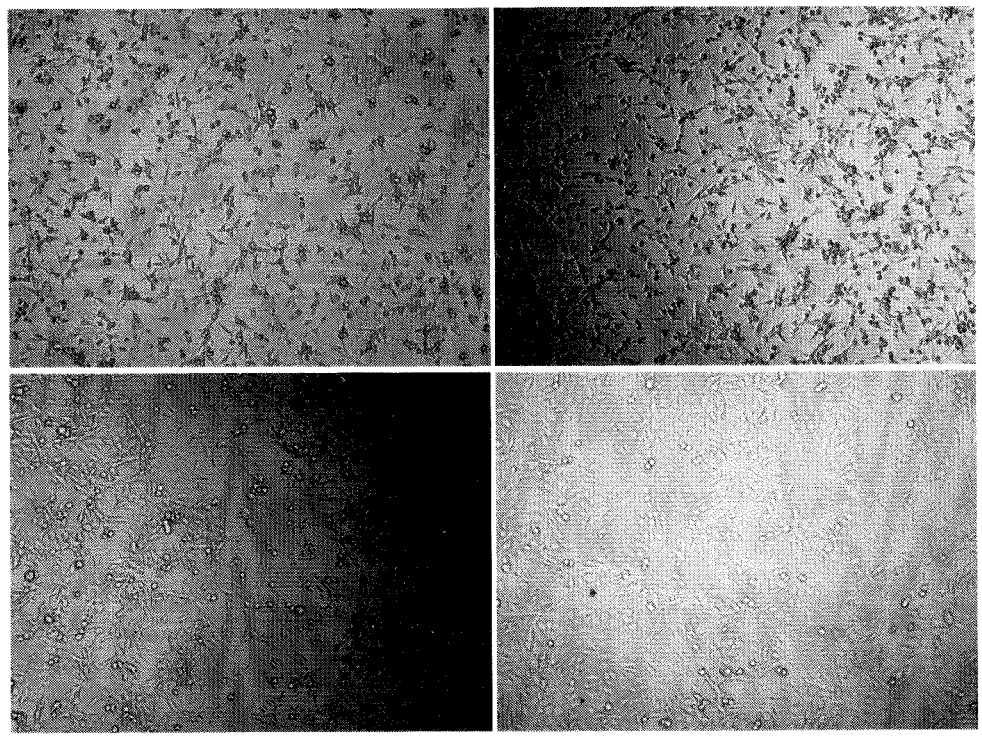
FIG. 1. Microphotographs of C2C12 cell on LA2 polystyrene. Murine myoblast C2C12 cells were seeded on uncoated polystyrene (A), or polystyrene coated 0.05-(B), 0.2-(C), and 0.4 (D) μg/ml LA2. Three hours after cell seeding, the materials were washed with PBS and micrographs taken with phase contrast optics. Original magnification 200×.

In one embodiment each multi-domain peptide of the invention contains two substantially similar sequences (homodimeric sequences) that are derived from or analogs of a portion of a laminin cell binding motif. The homodimeric sequences may be derived from any portion of laminin. The multi-domain peptide further includes a heparin-binding peptide sequence, preferably covalently bonded to the homodimeric sequence, and more preferably covalently bonded to the homodimeric sequence by means of a linker sequence, which linker sequence in turn is preferably a hydrophobic linker sequence.

Thus in one aspect the invention provides a synthetic, multi-domain peptide containing cell attachment domains, preferably IKVAV (SEQ ID NO:2), together with a heparin-binding domain that improves cell adhesion. In a related aspect there is further included a hydrophobic domain, which among other advantages imparts the ability for the multi-domain peptide to be readily adsorbed onto many implant surfaces. In part the multi-domain peptide of the invention mimics the localization of IKVAV (SEQ ID NO:2) and the heparin binding domain of laminin on the α chain of laminin.

As provided herein, the multi-domain peptides of the present invention can be used as a coating for medical devices, and can also and further be employed for improved cell attachment in vitro and tissue integration in vivo. Thus the multi-domain peptides of the present invention may be employed as a part or component of a medical device, as an adjunct or reagent for use in cell culture and other in vitro methods, and as a pharmaceutical product, such as for promotion of tissue integration in a patient.

The multi-domain peptides of formulas I to V: The regions X and Z of the synthetic multi-domain peptides of formulas I to V include amino acid residues, and optionally the region Y includes amino acid residues. An amino acid residue is defined as —NHRCO—, where R can be hydrogen or any organic group. The amino acids can be D-amino acids or L-amino acids. Additionally, the amino acids can be α-amino acids, β-amino acids, γ-amino acids, or δ-amino acids and so on, depending on the length of the carbon chain of the amino acid.

The amino acids of the X, Y and Z component regions of the synthetic multi-domain peptides of the invention can include any of the twenty amino acids found naturally in proteins, i.e. alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine, (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Furthermore, the amino acids of the X, Y and Z component regions of the synthetic multi-domain peptides of the invention can include any of the naturally occurring amino acids not found naturally in proteins, e.g. β-alanine, betaine (N,N,N-trimethylglycine), homoserine, homocysteine, γ-amino butyric acid, ornithine, and citrulline.

Additionally, the amino acids of the X, Y and Z component regions of the synthetic multi-domain peptides of the invention can include any of the non-biological amino acids, i.e. those not normally found in living systems, such as for instance, a straight chain amino carboxylic acid not found in nature. Examples of straight chain amino carboxylic acids include 6-aminohexanoic acid, 7-aminoheptanoic acid, 9-aminononanoic acid and the like.

In formula I, two X regions are covalently linked to $R_1$, either directly or through an $R_2$ group, where $R_1$ is a trifunctional amino acid residue, preferably a trifunctional alpha amino acid residue. It is to be appreciated that such covalent bonds may be to any chemically permitted functional group. Where the trifunctional amino acid residue is an amino acid with a reactive sulfhydryl side chain, such as cysteine, it is possible and contemplated that one X is covalently bonded through the N-terminus amine group, the second X is covalently bonded through the reactive sulfhydryl side chain, such as where $R_2$ includes a second cysteine residue covalently liked through a disulfide bond, and Y is covalently bonded to the second cysteine through the C-terminus carboxyl group thereof.

In a particularly preferred embodiment, $R_1$ is a diamine trifunctional amino acid residue, wherein $R_1$ is covalently bonded to Y through the carboxyl group of $R_1$, and the two X groups are covalently bonded to $R_1$ through the alpha amine and the epsilon amine of the side chain. Preferred groups for $R_1$ thus include 2,3 diamino propionyl amino acid, 2,4 diamino butylic amino acid, lysine and ornithine.

Particularly useful amino acid sequences as X regions of formulas I to V include homologs of fragments of naturally occurring laminin-derived speptides that differ from the amino acid sequences of laminin-derived peptides in only one or two or a very few positions. Such sequences preferably include conservative changes, where the original amino acid is replaced with an amino acid of a similar character according to well known principles; for example, the replacement of a non-polar amino acid such as alanine with valine, leucine, isoleucine or proline; or the substitution of one acidic or basic amino acid with another amino acid of the same acidic or basic character.

In another alternative, the X regions of the multi-domain peptide can include an amino acid sequence that shows no detectable homology to the amino acid sequence of any laminin or basement membrane peptide. Peptide sequences useful as components of the X region of the multi-domain peptides of the present invention, that have little or no amino acid sequence homology with known laminin or basement membrane peptides and yet increase cell adhesion and tissue integration may be obtained by any of a wide range of methods, including for instance, selection by phage display. See as an example: Sidhu et al. Phage display for selection of novel binding peptides. Methods Enzymol. 328:333-63 (2000).

The X region of the synthetic multi-domain peptides of the invention can have any length that includes an amino acid sequence that effectively promotes cellular attachment, adhesion, differentiation or the like. Preferably, the X regions of the synthetic multi-domain peptides have a minimum length of at least approximately three amino acid residues. More preferably, the X regions of the synthetic multi-domain peptides have a minimum length of at least approximately five amino acid residues. The X regions of the synthetic multi-domain peptides of the invention preferably also have a maximum length of up to approximately fifty amino acid residues, more preferably a maximum length of up to approximately twenty amino acid residues, and most preferably a maximum length of up to approximately ten amino acid residues.

The $R_2$ regions of formulas I, III, IV or V can include a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non natural amino acids, such as amino hexanoic acid; or a combination of any of the foregoing amino acids). It is also contemplated that agents such as polyethylene glycol (PEG), polyethylene oxide (PEO), amino polyethylene glycol, bis-amine-PEG, and other variants of polyethylene glycol known to those skilled in the art can similarly be used.

The chain of atoms of the $R_2$ region formulas I, III, IV or V is covalently attached to X and $R_1$. The covalent bonds can be, for example, a peptide bond or other amide bond, or a thioether or ester bond. If present, the $R_2$ region preferably includes a chain of a minimum of about three backbone atoms. For example, where the covalent bonds are peptide bonds, the $R_2$ region may be formed from a chain of at least one, at least two or at least three amino acids. However, where other than peptide bonds are employed, the $R_2$ region may further include a cross-linking moiety. For example, where $R_1$ is Cys or another trifunctional amino acid with a reactive sulfhydryl, the $R_2$ region can be a linker consisting of a sulfhydryl reactive homo-bifunctional cross linker and a second Cys, or alternatively can include a hetero-bifunctional cross-linker, such as a cross-linker linking to the sulfhydryl on the $R_1$ side chain and carboxyl group of X.

In the synthetic multi-domain peptides of the present invention, in one preferred embodiment the Y region of any of formulas I to V is a linker that is sufficiently hydrophobic to non-covalently bind the multi-domain peptide of the present invention to a polystyrene or polycaprolactone surface, or the like. In addition, the Y region may bind to other hydrophobic surfaces, particularly the hydrophobic surfaces formed from materials used in medical devices. Such surfaces are typically hydrophobic surfaces. Examples of suitable surfaces include but are not limited to those formed from hydrophobic polymers such as polycarbonate, polyester, polypropylene, polyethylene, polystyrene, polytetrafluoroethylene, expanded polytetrafluoroethylene, polyvinyl chloride, polyamide, polyacrylate, polyurethane, polyvinyl alcohol, polyurethane, poly ethyl vinyl acetate, poly(butyl methacrylate), poly(ethylene-co-vinyl acetate), polycaprolactone, polylactide, polyglycolide and copolymers of any two or more of the foregoing; siloxanes such as 2,4,6,8-tetramethylcyclotetrasiloxane; natural and artificial rubbers; glass; and metals including stainless steel, titanium, platinum, and nitinol. Preferably, the binding of the multi-domain peptides to the hydrophobic surface is of sufficient quantity to be detected by an analytical method such as an enzyme-linked immunoassay or a biological assay.

According to one embodiment of the invention, the Y region of formulas I to V includes a chain of atoms or a combination of atoms that form a chain. Typically, the chains are chains of carbon atoms, that may also optionally include oxygen, nitrogen or sulfur atoms, such as for example chains of atoms formed from amino acids (e.g., amino acids found in proteins, as listed above; naturally occurring amino acids not found in proteins, such as ornithine and citrulline; or non-natural amino acids, such as straight chain amino carboxylic acid; or a combination of any of the foregoing amino acids).

The chain of atoms of the Y region of formula I to V is covalently attached to $R_1$ and to peptide Z. The covalent bonds can be, for example, peptide, amide, thioether or ester bonds. Preferably, the Y region includes a chain of a minimum of about nine backbone atoms. More preferably, the Y region includes a chain of a minimum of about twelve atoms. Most preferably, the Y region includes a chain of a minimum of about fifteen atoms. For example, the Y region may be formed from a chain of at least four, at least five or at least six amino acids. Alternatively, the Y region may be formed from a chain of at least one, at least two, or at least three aminohexanoic acid residues.

Preferably, the Y region includes a chain of a maximum of about fifty atoms. More preferably, the Y region includes a chain of a maximum of about forty-five atoms. Most preferably, the Y region includes a chain of a maximum of about thirty-five atoms. For example, the Y region may be formed from a chain of up to about twelve, up to about fifteen, or up to about seventeen amino acids.

In a particular embodiment, the Y region includes a hydrophobic amino acid residue, or a chain of hydrophobic amino acid residues. The Y region can, for example, include one or more straight chain amino carboxylic acids, such as for example aminohexanoic acid residues, such as one, two, three or more aminohexanoic acid residues. Alternatively, the Y region can include up to about twelve, up to about fifteen, or up to about seventeen ethylene glycol residues. In another alternative embodiment, the Y region can include a combination of amino acid hydrophobic residues.

In another particular embodiment, the Y region of the molecule can include a branched or unbranched, saturated or unsaturated alkyl chain of between one and about twenty carbon atoms. In a further embodiment, the Y region can include a chain of hydrophilic residues, such as for instance, ethylene glycol residues. For instance, the Y region can include at least about three, or at least about four, or at least about five ethylene glycol residues.

The Z region of the molecule of formula I is a heparin-binding region and can include one or more heparin-binding motifs, BBxB or BBBxxB as described by Verrecchio et al. J. Biol. Chem. 275:7701 (2000). Alternatively, the Z region can include both BBxB and BBBxxB motifs (where B represents lysine, arginine, or histidine, and x represents a naturally occurring, or a non-naturally occurring amino acid). For example, the heparin-binding motifs may be represented by the sequence [KR][KR][KR]X(2)[KR] (SEQ ID NO:19), designating the first three amino acids as each independently selected from lysine or arginine, followed by any two amino acids and a sixth amino acid which is lysine or arginine.

The number of heparin binding motifs is variable. For instance, the Z region may include at least one, at least two, at least three or at least five heparin-binding motifs. Where there are more than one heparin-binding motifs, the motifs may be the same or different. Alternatively, the Z region includes up to a maximum of about ten heparin-binding motifs. In another alternative embodiment, the Z region includes at least four, at least six or at least eight amino acid residues. Further, in certain embodiments the Z region includes up to about twenty, up to about, twenty-five, or up to about thirty amino acid residues. It is to be realized that, in part, the avidity of the Z region for heparin is determined by the particular heparin-binding motifs selected and the number of such motifs in Z. Thus for particular applications both the selection and number of such motifs may be varied to provide optimal heparin binding of the Z region.

In one preferred embodiment, the amino acid sequence of the Z region is RKRKLERIAR (SEQ ID NO20). In another embodiment, the amino acid sequence of the Z region is RKRKLGRIAR (SEQ ID NO:21). In yet another embodiment, the amino acid sequence of the Z region is RKRKLWRARA (SEQ ID NO:22). In yet another embodiment, the amino acid sequence of the Z region is RKRLDRIAR (SEQ ID NO:23), providing a heparin-binding motif derived from a modification of the sequence at residues 270-279 of the Jun/AP-1 DNA binding domain (Busch et al. Trans-Repressor Activity of Nuclear Glycosaminoglycans on Fos and Jun/AP-1 Oncoprotein-mediated Transcription. J. Cell Biol. 116: 31-42, 1992). In yet another embodiment, the amino acid sequence of the Z region is RKRKLERIARC (SEQ ID NO:24). The presence of a terminal cysteine residue optionally affords the opportunity to link other molecules, molecules, including detection reagents such as fluorochromes, radioisotopes and other detectable markers, to the Z region, as well as the opportunity to link toxins, immunogens and the like.

Heparin-binding domains that bear little or no sequence homology to known heparin-binding domains are also contemplated in the present invention. As used herein the term "heparin-binding" means binding to the —$NHSO_3^-$ and sulfate modified polysaccharide, heparin, and also binding to the related modified polysaccharide, heparan. Such domains are contemplated to exhibit binding in physiological solutions including 0.15 M NaCl, and are expected to uncomplex at salt concentrations greater than about 0.5 M NaCl.

The Z region of the multi-domain peptides of the present invention confers the property of binding to heparin in low salt concentrations, up to about 0.15 M NaCl, optionally up to about 0.48 M NaCl, forming a complex between heparin and the Z region of the multi-domain peptides. The complex can be dissociated in great than about 0.5 M NaCl, such as 1 M NaCl, to release the multi-domain peptide from the heparin complex.

The Z region is a non-signaling peptide. Accordingly, when used alone the Z region binds to heparin, but the binding of the Z region peptide alone does not initiate or block signaling by any receptor.

The C-terminus of the Z region may be blocked or free. For example, the C terminus of the Z region may be the free carboxyl group of the terminal amino acid, or alternatively, the C terminus of the Z region may be a blocked carboxyl group, such as for instance, an amide group.

DEFINITIONS

As used here and elsewhere, the following terms have the meanings given.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical—$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C=O)—} groups. A peptide is most usually acylated at the N-terminus.

An "amide" includes compounds that have a trivalent nitrogen attached to a carbonyl group (—$CO.NH_2$).

An "amine" includes compounds that contain an amino group (—$NH_2$).

A "diamine amino acid" is an amino acid or residue containing two reactive amine groups and a reactive carboxyl group. Representative examples include 2,3 diamino propionyl amino acid, 2,4 diamino butylic amino acid, lysine or ornithine.

The term "homologous", as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, 20% or 25% of the amino acid residues when the amino acid sequences of the two peptide homologs are aligned.

A "trifunctional amino acid" is an amino acid or residue with three reactive groups, one the N-terminus amine, a second the C-terminus carboxyl, and the third comprising all or a part of the side chain. Trifunctional amino acids thus include, by way of example only, diamine amino acids; amino acids with a reactive sulfhydryl group in the side chain, such as mercapto amino acids including cysteine, penicillamine, or 3-mercapto phenylalanine; amino acids with a reactive carboxyl group in the side chain, such as aspartic acid and glutamic acid; and amino acids with a reactive guanadium group in the side chain, such as arginine.

In one embodiment, there is provided a multi-domain peptide referred to herein as LA2. LA2 is a multi-domain, synthetic peptide containing a laminin-derived cell attachment domain, IKVAV (SEQ ID NO:2) together with a heparin-binding domain linked by means of a hydrophobic sequence. A substrate coating of LA2 results in significant enhancement of cell attachment and cell growth in vitro. A coating of LA2 also supports the attachment of the osteoprogenitor cell line MC3T3-E1 and enhances its expression of alkaline phosphatase, suggesting an enhancement of osteo-differentiation. As a coating LA2 enhances cell attachment on materials commonly used in medical implants including ePTFE and titanium. In vivo following subcutaneous implant, LA2 coated ePTFE had substantially more tissue integration into the implant as compared to uncoated material.

The invention thus provides a synthetic peptide containing homodimeric cell attachment domains such as IKVAV (SEQ ID NO:2) plus a heparin binding domain, thereby providing for improved cell adhesion compared to the use of simple binding motifs. The design of LA2 as a multi-domain peptide in part is intended to mimic aspects of the carboxy-terminal portion of α-chain of laminin that contains the IKVAV (SEQ ID NO:2) sequence and heparin-binding sequences. (Charonis et al., A novel synthetic peptide from the B1 chain of laminin with heparin-binding and cell adhesion-promoting activities. J Cell Biol 107 (1988) 1253-60). The heparin binding domain RKRKLERIAR (SEQ ID NO:20) was selected as it conforms to a canonical XBBBXXBX heparin-binding motif although it does not occur in laminin. (Verrecchio et al., Design of peptides with high affinities for heparin and endothelial cell proteoglycans. J Biol Chem 275 (2000) 7701-7). Two copies of IKVAV (SEQ ID NO:2) were used in LA2 with the goal of improving the apparent affinity of the peptide for its receptor. LA2 also contains a hydrophobic domain bridging the heparin binding domain and IKVAV (SEQ ID NO:2) sequences. The hydrophobic domain contributes to an enhanced substrate coating or binding, compared to other peptides lacking a hydrophobic domain or other subcomponents of LA2.

In certain aspects, the laminin-derived multi-domain peptides of the invention have similarities to growth factor constructs which include a heparin-binding domain. (Lin et al. Synthetic peptide F2A4-K-NS mimics fibroblast growth factor-2 in vitro and is angiogenic in vivo. International Journal of Molecular Medicine 17 (2006) 833-841; Lin et al. Multi-domain Synthetic Peptide B2A2 Synergistically Enhances BMP-2 In Vitro. J Bone Miner Res 20 (2005) 693-703. See also U.S. Published Patent Application 2004/0038348, published Feb. 26, 2004, and U.S. Published Patent Application 2004/0087505, published May 6, 2004, incorporated herein by reference.

LA2 is highly effective in enhancing cell attachment. Also effective, though not as effective as LA2, is a similar multi-domain peptide containing YIGSR (SEQ ID NO:1), hereafter "MD Peptide 2." Both LA2 and MD Peptide 2 were more effective than the linear peptide SIKVAV (SEQ ID NO:16), a dimerized SIKVAV (SEQ ID NO:16) and peptides with random sequences introduced into the cell attachment domain. LA2 was similar to laminin and fibronectin in supporting cell attachment.

When used as competitive blocking agents, both heparin and SIKVAV (SEQ ID NO:16) reduced the level of cell binding. However, neither heparin nor SIKVAV (SEQ ID NO:16) eliminated cell binding when used individually, suggesting that both the IKVAV (SEQ ID NO:2) and the heparin binding domains of LA2 contribute to cell attachment. The suggestion that both IKVAV (SEQ ID NO:2) and heparin-binding domains contribute to cell attachment is strengthened by observations that peptides with heparin binding domains but without SIKVAV (SEQ ID NO:16) fail to enhance cell attachment.

Laminin and other extracellular matrix molecules are known to contribute to differentiation. (Kleinman et al. The laminins: a family of basement membrane glycoproteins important in cell differentiation and tumor metastases. Vitam Horm 47 (1993) 161-86). LA2, which is designed to mimic certain aspects of laminin, was found to contribute to the differentiation of osteoblast progenitor cells as monitored by increase in alkaline phosphates following stimulation by BMP-2. This is hypothesized to be consistent with a report of a convergence of bone morphogenetic protein and laminin-1 signaling pathways. (Jiang and Harrison. Convergence of bone morphogenetic protein and laminin-1 signaling pathways promotes proliferation and colony formation by fetal mouse pancreatic cells. Exp Cell Res 308 (2005) 114-22). At least one other peptide coating based on an extracellular matrix molecule, P-15, may also contribute to signal transduction and differentiation.

LA2 is hypothesized to interact with surfaces via hydrophobic interaction. LA2 bound to all substrates tested, including polystyrene, polycarbonate, EVA, stainless steel, titanium, and ePTFE. Stainless steel, titanium and ePTFE are widely used in the construction of implantable medical devices. ePTFE has been used in applications ranging from vascular implants to dental implants. (Zdrahala. Small caliber vascular grafts. Part I: state of the art. J Biomater Appl 10 (1996) 309-29; Carpio, et al. Guided bone regeneration around endosseous implants with anorganic bovine bone mineral. A randomized controlled trial comparing bioabsorbable versus non-resorbable barriers. J Periodontol 71 (2000) 1743-9; Wikesjo et al. Space-providing expanded polytetrafluoroethylene devices define alveolar augmentation at dental implants induced by recombinant human bone morphogenetic protein 2 in an absorbable collagen sponge carrier. Clin Implant Dent Relat Res 5 (2003) 112-23; Wikesjo et al. Periodontal repair in dogs: space-providing ePTFE devices increase rhBMP-2/ACS-induced bone formation. J Clin Periodontol 30 (2003) 715-25).

High porosity ePTFE was used as an example of an implant that typically does not support cell attachment. The high porosity allowed facile monitoring of tissue integration. LA2 significantly improved tissue integration into ePTFE when implanted subcutaneously in rats, demonstrating that the peptide coating was at least permissive, and presumptively stimulatory, for cell migration in vivo.

LA2, and other laminin-derived multi-domain peptides of this invention, may be employed to improve in vivo cell attachment and differentiation on a range of implants. In one aspect, LA2 is applied to ePTFE vascular graft material. By stimulating tissue integration throughout a graft or other implant by means of LA2 and other laminin-derived multi-domain peptides of this invention, the resulting enhanced tissue integration can supply a renewable endothelial source leading to more durable endothelial lining. Similarly, LA2 and other laminin-derived multi-domain peptides of this invention can be applied to porous titanium implants to provide an accelerated tissue integration of bone cells into the implant. This directly results in a more solidly anchored implant.

LA2, and other laminin-derived multi-domain peptides of this invention, may be employed to therapeutically induce angiogenesis or to augment angiogenesis induced by other pharmacologic agents including growth factors and analogs and mimetics thereof. By pharmacologically inducing angiogenesis, the LA2 may be used to enhance the survival of transplanted cells and tissue or to repair damaged tissue after an ischemic event. In a further aspect, LA2, and other laminin-derived multi-domain peptides of this invention, may be implanted in proteinacious matrixes such as collagen or in hydrogels, including those made of hyaluronic acid, carboxymethylcellulose, and the like. LA2, and other laminin-derived multi-domain peptides of this invention, may also be locally administered into the body via subcutaneous, intramuscular, intrathecal, or similar routes.

Methods of synthesizing the multi-domain peptides of the invention: The synthesis of the multi-domain peptides of the invention can be achieved by any of a variety of chemical methods well known in the art. Such methods include bench scale solid phase synthesis and automated peptide synthesis in any one of the many commercially available peptide synthesizers. Preferably, the synthesizer has a per cycle coupling efficiency of greater than 99 percent.

The analogs of the present invention can be produced by stepwise synthesis or by synthesis of a series of fragments that can be coupled by similar well known techniques. See, for instance, Nyfeler, Peptide synthesis via fragment condensation. Methods Mol. Biol. 35:303-16 (1994); and Merrifield, Concept and early development of solid-phase peptide synthesis. Methods in Enzymol. 289:3-13 (1997). These methods are routinely used for the preparation of individual peptides. It is alternatively possible to assemble the analogs of the present invention in component parts, such as peptides constituting the X, Y and Z components thereof, and to thereafter couple such component parts to assemble the analog. See, for instance, Dawson and Kent, Synthesis of native proteins by chemical ligation. Annu. Rev. Biochem. 69:923-960 (2000); and Eom et al., Tandem ligation of multipartite peptides with cell-permeable activity. J. Am. Chem. Soc. 125:73-82 2003). However, in a preferred embodiment the compounds of the present invention are synthesized by solid phase synthesis, with the C-terminus residue of the Z region of formulas I to V bound to resin, and the synthesis proceeding stepwise. Conventional protecting groups are employed as required, with deprotection either prior to, during or following cleavage of the peptide from the resin. By way of example only, for compounds of the present invention containing one or more lysine residues in addition to that at the $R_1$ position of formula I, such additional lysine residues will conventionally be protected with a protecting group, and deprotected following synthesis.

In a particular embodiment, the synthetic multi-domain peptide of the invention is derived from laminin.

In a particular aspect, the invention provides a method for stimulating cellular adhesion, including one or more of cell attachment or differentiation, to a surface by contacting the surface with an effective amount of a multi-domain peptide according to formulas I to V. The effective amount can be readily determined by one of skill in the art.

Methods of use of the multi-domain peptides of the invention: The multi-domain peptides of the invention provide a cost effective and potentially unlimited source of biologically active molecules that are useful in a number of ways, including as biologically active agents for coating of medical devices, such as for instance, sutures, implants and medical instruments to promote biological responses, for instance, to stimulate growth and proliferation of cells, or healing of wounds.

In one aspect, the invention provides a method and compositions for treating a mammal with bone injury, by providing a multi-domain peptide of the present invention. For example, such multi-domain peptides of the present invention may be administered as a pharmaceutical agent, or may be employed as an additive to bone matrix or bone graft materials.

In another aspect, the invention provides a method and compositions for preparation of cell or organ implant sites. In one embodiment, a multi-domain peptide of the present invention is administered by a percutaneous route to stimulate localized angiogenesis prior to implant of insulin-secreting pancreatic cells, and thereby improve the survival of the implanted cells. Similarly, a multi-domain peptide of the present invention is administered into ischemic heart tissue prior to the implant of myocte stem cells.

In another aspect, the invention provides a method and compositions to increase cellular attachment to and cellular retention on blood-contacting surfaces of medical devices. In one embodiment, a multi-domain peptide of the present invention is applied on vascular graft materials such that the bound analog recruits and binds circulating endothelial stem cells from the blood, thereby resulting in endothelialization of the graft surface with resultant long-term thromboresistance being imparted to the graft.

In another aspect, the invention provides a method and compositions to increase and provide for membrane-guided tissue growth.

In another aspect, the invention provides a method and composition for treatment of difficult-to-treat dermal wounds, including ulcers. In one embodiment, a multi-domain peptide is applied topically in a pharmaceutically acceptable cream or gel for treatment of ulcerated bed sores and similar difficult-to-treat dermal wounds.

In yet another aspect, the invention provides a method and compositions to selectively increase cellular populations in vitro. For example, a multi-domain peptide is formulated in a tissue culture medium to specifically stimulate the growth of endothelial cells.

The term "medical device" as used herein means a device that has one or more surfaces in contact with an organ, tissue, blood or other bodily fluid in an organism, preferably a mammal, particularly, a human. Medical devices include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body, such as vascular grafts, stents, pacemaker leads, heart valves, and the like that are implanted in blood vessels or in the heart. The term can further include devices for temporary intravascular use such as catheters, guide wires, and the like that are placed in blood vessels or the heart for purposes of monitoring or repair. The term can further include nerve electrodes, muscle electrodes, implantable pulse generators, implantable drug pumps, and defibrillators. Moreover, the term medical device can include sutures, graft materials, wound coverings, nerve guides, bone wax, aneurysm coils, embolization particles, microbeads, dental implants, bone prostheses, tissue scaffolds, artificial joints or controlled release drug delivery devices.

The surface of the medical device can be formed from any of the commonly used materials suitable for use in medical devices, such as for instance, stainless steel, titanium, platinum, tungsten, ceramics, polyurethane, polytetrafluoroethylene, extended polytetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide, polysiloxanes (such as 2,4,6,8-tetramethylcyclotetrasiloxane), natural rubbers, or artificial rubbers, or block polymers or copolymers thereof.

Methods for coating biological molecules onto the surfaces of medical devices are known. See for instance U.S. Pat. No. 5,866,113 to Hendriks et al., the specification of which is hereby incorporated by reference. Tsang et al. in U.S. Pat. No. 5,955,588 teach a non-thrombogenic coating composition and methods for using the same on medical devices, and is incorporated herein by reference. Zamora et al. in U.S. Pat. No. 6,342,591 teach an amphipathic coating for medical devices for modulating cellular adhesion composition, and is incorporated herein by reference.

In one embodiment, the invention provides a method for delivering an active peptide to a mammal, the method includes (i) providing a medical device coated on its surface with a multi-domain peptide of formulas I to V, the multi-domain peptide being bound to the surface of the medical device by non-covalent bonds; and (ii) placing the medical device onto a surface of, or implanting the medical device into, the mammal.

In a particular embodiment of the above method, the non-covalent bonds are associations between the heparin binding domain of the multi-domain peptide and a heparin-containing compound bound to the surface of the medical device. The heparin-containing compound bound to the surface of the medical device can be any heparin-containing compound, such as for instance, benzyl-bis(dimethylsilylmethyl)oxy carbamoyl-heparin.

In another particular embodiment of the above method, the medical device is not pre-coated with a heparin-containing compound before being coated with the multi-domain peptide of formulas I to V.

Multi-Domain Peptide Pharmaceutical Applications: The multi-domain peptides of this invention can be used for as an active ingredient in pharmaceutical compositions for both medical applications and animal husbandry or veterinary applications. Typically, the multi-domain peptide or pharmaceutical composition is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

The multi-domain peptides of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the multi-domain peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the multi-domain peptides of this invention are prepared in a suitable solvent for the multi-domain peptide and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the multi-domain peptides of this invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a multi-domain peptide of this invention and a pharmaceutically acceptable carrier. The carrier may be a liquid formulation, and in one embodiment a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Thus the multi-domain peptide compositions of this invention may be formulated or compounded into pharmaceutical compositions that include at least one multi-domain peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, PEG, PEO, mannitol, sodium chloride or sodium citrate, as well as any number of simple sugars, including sucrose, dextrose, lactose and the like, and combinations of the foregoing. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a multi-domain peptide of this invention over a period of time.

In practical use, the multi-domain peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

If the multi-domain peptide pharmaceutical composition is administered by injection, the injection may be intravenous, subcutaneous, intramuscular, intraperitoneal or other means known in the art. The multi-domain peptides of this invention may alternatively be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the multi-domain peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

In general, the actual quantity of multi-domain peptide of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect.

EXAMPLE 1

Peptide Synthesis. Peptides in milligram quantities were synthesized manually following standard Fmoc protocols using NovaSyn TGR resin (EMD BioSciences, La Jolla, Calif.). Fmoc-amino acids including aminohexanoic acid (Ahx) were obtained from Peptides International, Inc. (Lexington, Ky.). LA2 contains two copies of the laminin-derived sequence IKVAV (SEQ ID NO:2) derived from native laminin (residues 2100-2104), and a heparin binding domain, RKRKLERIAR (SEQ ID NO:20), that conforms to the canonical XBBBXXBX heparin-binding motif (X represent any amino acid residue and B represent basic amino acid residues). LA2 was synthesized as a branched peptide with the following sequence H-SIKVAVAAK(H-SIKVAVAA)-Ahx-Ahx-Ahx-RKRKLERIAR-NH$_2$. It was purified by RP-HPLC on a C18 column, using a linear gradient 0-60% acetonitrile/water (0.1% trifluoroacetic acid) run over 60 min at 3 ml/min flow rate (detection at 214 nm). The purified peptide generated a single uniform peak on analysis by RP-HPLC. Software associated with the HPLC (Shimadzu Scientific Instruments, Inc., Columbia, Md.) was used to determine the percent area under the peptide peak. The theoretical molecular weight of LA2 is 3272 Daltons.

MD Peptide 2 was similarly synthesized, but contained the laminin-derived sequence YIGSR (SEQ ID NO:1). The sequence of MD Peptide 2 was H-YIGSRAAK(H-YIGSRAA)-Ahx-Ahx-Ahx-RKRKLERIAR-NH$_2$.

Two negative control multi-domain peptides were also synthesized, each containing an irrelevant homodimeric branched sequence with a -Ahx-Ahx-Ahx-hydrophobic linker sequence and a heparin binding domain, RKRKLERIAR (SEQ ID NO:20). In one multi-domain peptide the homodimeric branched sequence was KPVSLSYRA-PARFFESHVA (SEQ ID NO:25) and in the other the sequence was DTAYKDWPNLFREIR (SEQ ID NO:26), each random sequences.

EXAMPLE 2

Materials and Cell Lines. C2C12 (pluripotent murine myoblast), C3H10T1/2 (murine fibroblast), A7R5 (rat smooth muscle cells), MC3T3-E1 (murine pre-osteoblast), and 4MBr5 (monkey lung epithelial cells) were obtained from the American Type Culture Collection (Manassas, Va.). RMEC (rat microvascular endothelial cells transformed by SV40 Large T-antigen) were a gift from M. Goligorsky, Division of Nephrology and Hypertension, State University of New York at Stony Brook. (Tsukahara, et al. Molecular and functional characterization of the non-isopeptide-selective ETB receptor in endothelial cells. Receptor coupling to nitric oxide synthase. Biol Chem 269 (1994) 21778-85; and Tsukahara et al. Direct demonstration of insulin-like growth factor-1-induced nitric oxide production by endothelial cells. Kidney Int 45 (1994) 598-604). BAEC (bovine aortic endothelial cells) were obtained from Cambrex (East Rutherford, N.J.). All cells were cultured in a 37° C. incubator with a humidified atmosphere containing 5% $CO_2$. C2C12, C3H10T1/2, A7R5, RMEC, and 4MBr5 were grown in DMEM:F12 medium containing 10% newborn calf serum and antibiotics. MC3T3-E1 cells were grown in α-MEM medium containing 10% newborn calf serum and antibiotics. BAEC were grown in Endothelial Cell Medium-2 (EGM®-2, Cambrex, East Rutherford, N.J.), supplemented with 5% FBS, and EGM-2 MV singlequots supplements (Cambrex, East Rutherford, N.J.). The linear peptide SIKVAV was obtained from Bachem (San Carlos, Calif.). Bovine collagen was obtained commercially (Vitrogen 100, Cohesion, Palo Alto, Calif.). Bovine fibronectin, and laminin (Engelbreth-Holm-Swarm murine sarcoma basement membrane) were purchased from SigmaAldrich.

EXAMPLE 3

Surface Coating. For coating of all substrates except calcium phosphate, LA2 was diluted into 10 mM $NaHCO_3$. For coating calcium phosphate, LA2 was diluted into water. Square chips (7×7 mm) composed of polycarbonate, ePTFE, titanium or stainless steel were used as substrates during coating. Disks of EVA film with diameters of 1 cm and thicknesses of 2 mil were also used. BioCoat Osteologic disk (BD Biosciences San Jose, Calif.) was used as calcium phosphate substrate. For coating, the test materials were placed in wells of a 24-well plate and submerged in LA2 solution and incubated in 37° C. for 30 minutes. Untreated polystyrene 96-well plate was coated in situ. At the end of coating, the materials were rinsed with water three times and air-dried. For use in vitro, most substrates were rendered aseptic by immersion in 70% isopropanol followed by rinsing in sterile water. ePTFE graft material was sterilized with ethylene oxide and coated aseptically. All coatings were performed using sterile-filtered LA2.

The presence of LA2 on the surface of the various materials was established by using o-phthaldialdehyde (OPA) or by ELISA employing a rabbit polyclonal antibody that appears to recognize epitopes near the aminohexanoic acid residues of LA2. (See for example Joys and Kim. o-Phthalaldehyde and the fluorogenic detection of peptides. Anal Biochem 94 (1979) 371-7).

EXAMPLE 4

Cells Adhesion and Proliferation on LA2 coated surfaces. To evaluate the effects of LA2-coating on cell attachment, untreated polystyrene 96-well plates were coated with LA2 in concentration indicated in figures. In the cases of EVA films, ePTFE and titanium, the materials were placed in 48- or 96-well plate and coated with 2 μg/ml of LA2. Cell suspension in density of $1 \times 10^6$/ml was added to the wells. After culturing the cells at 37° C. for 3 hours, the 96-well plates were washed with PBS twice. Cell number on the surface was determined using CyQuant® cell Proliferation Kit (Molecular Probes, Eugene, Oreg.). To detect cell adhesion on the titanium and ePTFE surfaces, cells were fixed with 4% buffered formalin and stained with bis-benzamide, viewed using fluorescence microscopy, and images recorded on digital media. In the cell proliferation studies, EVA films (6.5 mm diameter), similar to those used in the cell adhesion studies, were coated with 2 μg LA2/ml. The coated films were placed in untreated polystyrene 96-well plate and A7R5 cell suspension in density of $1 \times 10^5$/ml was added to the wells. After incubation of 3 hours, 3 and 7 days, the EVA films were transferred to a new 96-well plate and cell number on the film was determined using CyQuant® cell Proliferation Kit.

EXAMPLE 5

Alkaline phosphatase (ALP) assay. Assays for alkaline phosphatase were performed using mouse osteoprogenitor cell line MC3T3-E1. Cells were seeded on uncoated or LA2 (2 μg/ml) coated polystyrene. Twenty-four hours later, medium was replaced with αMEM, supplemented with 2% serum with or without 50 ng/ml BMP-2. At 4 days post induction, ALP activity was determined. Briefly, cells were washed once with phosphate-buffered saline (PBS) and lysed with 0.1% Triton X 100 and sonicated. ALP activity was measured using p-nitrophenylphosphate (PNPP) as substrate, incubating at 37° C., and absorbance (405 nm) read using a microplate spectrophotometer.

EXAMPLE 6

Tissue integration of LA2-coated material in rat implant model. Male SD rats were anesthetized using an intraperitoneal administration of ketamine (40 mg/kg) and xylazine (5 mg/kg). Excess hair was removed and sterile surgical sites were prepared on the lower back. Subcutaneous pouches, approximately 3 cm long, were made through a skin incision using a hemostat and blunt dissection. A wafer (1×1.5 cm) of porous ePTFE was introduced into a subcutaneous pouch. The pouches were positioned on the upper flanks on either side of the backbone, with one wafer coated with MD LA2 and the other wafer uncoated. After the implant, the incision was closed with stainless steel surgical clips. Animals were assigned to experiment groups randomly. Each animal received bilateral subcutaneous implants. There were 8 implant sites for each treatment. After 14 days, animals were euthanized and the ePTFE implants were surgically recovered and processed for subsequent staining with hemotoxylin and eosin.

EXAMPLE 7

LA2 was found to directly adhere to a variety of materials as shown in Table 1:

| Surface Material | LA2 on Surface | Detection Method |
|---|---|---|
| Polystyrene | + | E |
| EVA | + | E |
| Polycarbonate | + | E |
| ePTFE | + | F |
| Titanium | + | E |
| Stainless Steel | + | E |

Materials were coated for 30 minutes, rinsed in water, and air-dried. LA2 on the surface was detected by direct ELISA (E) or by a fluorescence assay using o-phthalaldehyde reagent (F).

EXAMPLE 8

Polystyrene was selected as a test surface because it is known to not support effective cell attachment. Coating polystyrene with LA2 resulted in a significant increase in cell attachment compared to uncoated polystyrene (FIG. 1A). The LA2 coating stimulated attachment of C2C12 cells to polystyrene in a dose-dependent manner (FIG. 1B-D, 2A). At low concentrations of LA2 (0.05- to 0.1 µg/ml), there was a low but statistically significantly increase in cell attachment. Cell attachment gradually increased as the coating concentration increased from 0.1 to 0.4 µg/ml. At concentrations of 0.4 µg/ml or higher there was no further increase in cell attachment. However, at concentrations of 0.4 µg/ml or higher the cells spread on the substrate whereas at lower concentrations, the cells did not effectively spread.

EXAMPLE 9

LA2, containing IKVAV (SEQ ID NO:2) was found to be 3-4 times more effective in mediating attachment of RMEC cells than a similar peptide construct, MD Peptide 2, containing YIGSR (SEQ ID NO:1). YIGSR is a different laminin adhesion sequence that has been used to increase cell attachment to device surfaces [33,34]. MD Peptide 2, while not as effective as LA2, was nonetheless substantially more effective than uncoated controls. At concentrations of 0.1 µg/ml, LA2 resulted in an increase in percentage cells bound on polystyrene at two hours of over 150%, while MD Peptide 2 resulted in an increase of over 50%, in both instances as a percentage of uncoated controls. Peptides with two different random sequences in the receptor binding domain, SEQ ID NO:25 and SEQ ID NO:26, did not support cell binding to the polystyrene surface. Since cells could bind to LA2 via cell surface heparan sulfate, the heparin binding domain of LA2 was blocked by coating peptide on substrate-adsorbed heparin. (Zamora et al. Local delivery of basic fibroblast growth factor (bFGF) using adsorbed silyl-heparin, benzyl-bis(dimethylsilylmethyl)oxycarbamoyl-heparin. Bioconjug Chem 13 (2002) 920-6. Attachment of RMEC cells persisted indicating that the IKVAV (SEQ ID NO:2) was key in mediating cell attachment.

EXAMPLE 10

Figure 2:
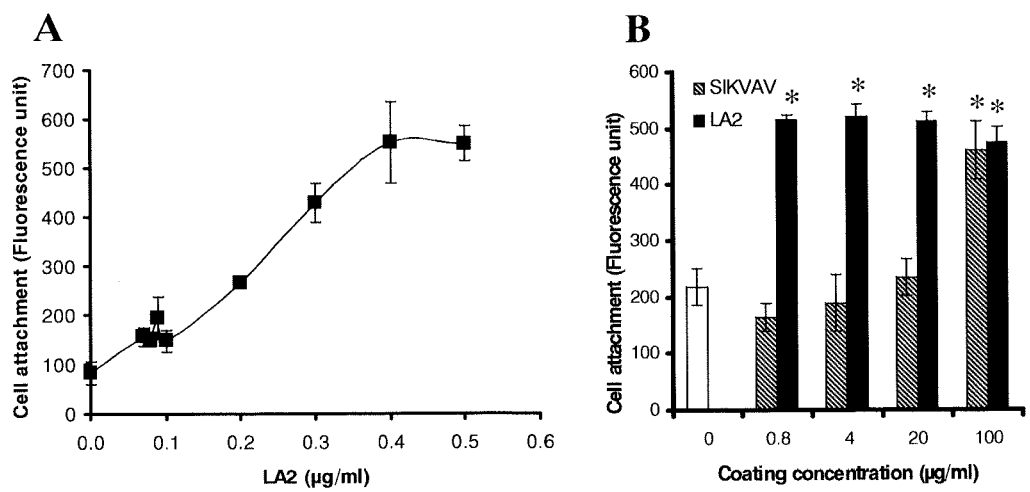
FIG. 2. Attachment of C2C12 cells to LA2 or SIKVAV (SEQ ID NO:16) coated polystyrene. C2C12 cells were seeded on polystyrene surface coated with LA2 (A) or SIKVAV (SEQ ID NO:16) (B). Three hours after seeding, unbound cells were removed by rinsing, and relative cell number determined using a fluorescent assay as described.

SIKVAV (SEQ ID NO:16) was used as a reference peptide based on reports, verified here, that it was able to increase cell attachment (FIG. 2B). However, substantially large amounts of SIKVAV (SEQ ID NO:16) (100 µg/ml) were required to achieved the same levels of cell attachment effects as produced by 0.4 µg/ml LA2. In studies designed to evaluate the relative effectiveness of LA2 as a coating, LA2 was more effective in supporting endothelial cell RMEC than similar peptides with YIGSR (SEQ ID NO:1) or random sequences introduced into the cell attachment domain. Additionally, a variant of LA2 synthesized without the heparin-binding domain of LA2 supported greater cell attachment than did SIKVAV (SEQ ID NO:16), although the number of cells bound was less than that of complete peptide LA2. In related cell binding assays LA2 was more effective in supporting cell attachment than bovine collagen and was as effective as intact laminin or fibronectin when used at the same coating concentration.

EXAMPLE 11

Figure 3:
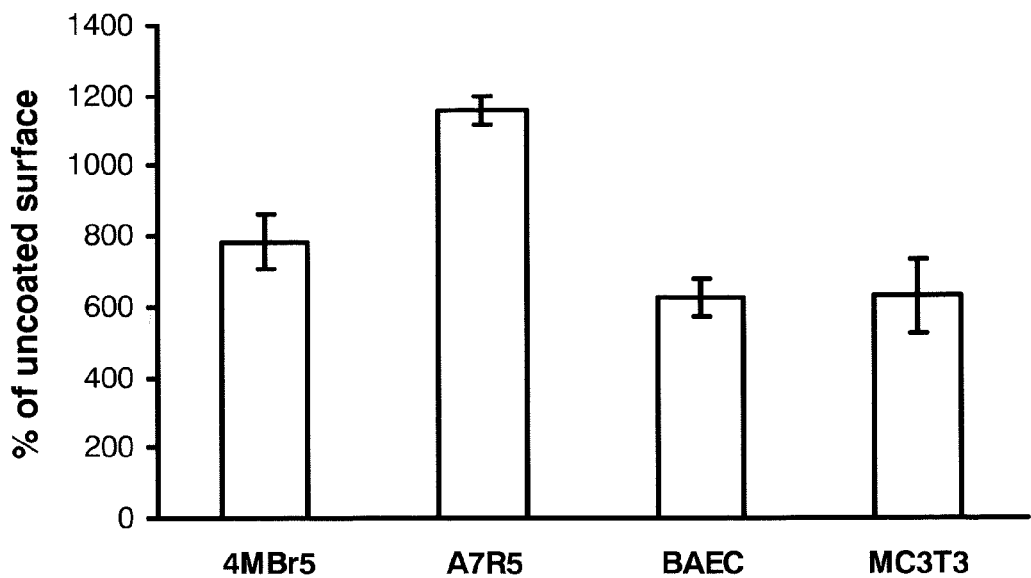
FIG. 3. The effect of LA2 coating on attachment of several cell types. Polystyrene surfaces were coated with 2 μg/ml LA2 peptide. Then A7R5, 4MBr5, BAEC and MC3T3 cells were seeded and incubated for 3 hours. At the end of the incubation, relative cell numbers were determined.

LA2 was effective in increasing the attachment of several different cell lines to polystyrene (FIG. 3). Cell attachment was increased for the smooth muscle cell line A7R5, the epithelial cell line 4MBr5, endothelial cells (BAEC) and MC3T3 osteoprogenitor cells.

EXAMPLE 12

Cells attached on the LA2 coated surfaces proliferated and formed confluent monolayers with morphologies similar to that observed on tissue culture plasticware. Using rat A7R5 cells, the cells seeded on LA2 coated EVA rapidly increased in cell number such that by day three the cells were confluent and remained so through day seven without apparent detachment. EVA normally does not support cell attachment and in control experiments A7R5 cells did not attach to EVA films.

EXAMPLE 13

Figure 4:
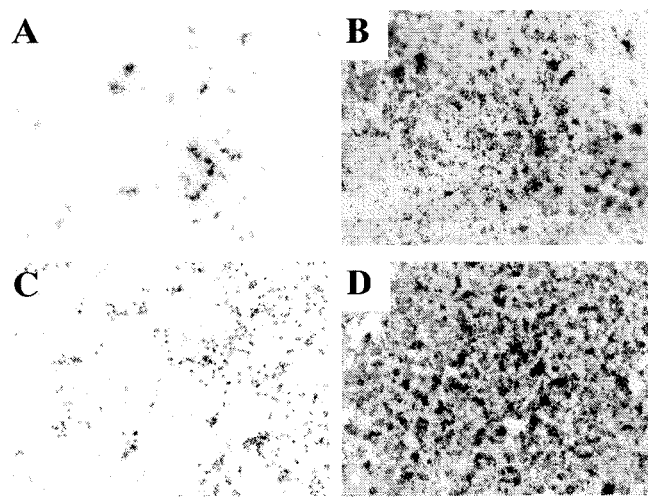
FIG. 4. The effects of LA2 coating on cell attachment on ePTFE and titanium surfaces. ePTFE (A and B) and titanium (C and D) surfaces were used as untreated (A and C) or were coated with 2 μg/ml LA2 peptide (B and D). C3H10T1/2 cells were seeded on to the surfaces and incubated for 3 hours. At the end of incubation, the surfaces were washed with PBS three times and fixed with 4% buffered formalin. Cells attached on the surfaces were visualized by fluorescence microscopy after stained with the nuclear stain bis-benzamide. Note the increased cell density revealed as darkly staining nuclei. (Original magnification: 100×).

LA2 enhanced cell attachment to ePTFE and titanium. With no coating, the cells attached very poorly to ePTFE or titanium as revealed by staining attached cells with bis-benzamide, a nuclear stain. However, ePTFE and titanium coated with LA2 had dramatically increased cell attachment (FIG. 4).

EXAMPLE 14

Figure 5:
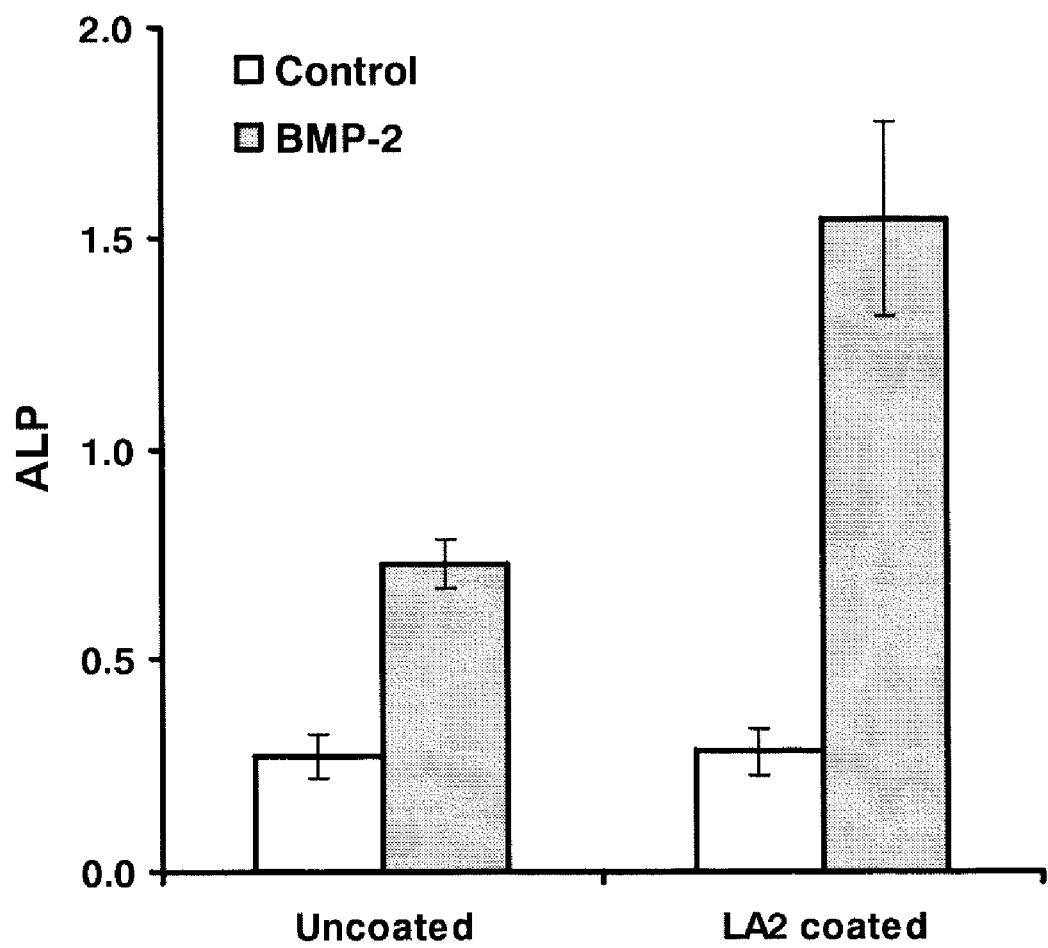
FIG. 5. The effect of LA2 coating on BMP-2-induced alkaline phosphatase in osteoprogenitor cells. C2C12 cells were seeded on uncoated or LA2 coated polystyrene surfaces. BMP-2 (50 ng/ml) was added 24 hours later. After 4 days, alkaline phosphatase activity was measured as described in method section. Data is presented as the average ±S.D. The asterisk indicates p<0.05 determined using t testing.

LA2 was found not only to support cell attachment and growth but also enhance cell differentiation as determined using MC3T3 cells. As shown in FIG. 5, LA2 enhanced alkaline phosphatase production in MC3T3 cells. Alkaline phosphatase is a widely used marker of osteo-differentiation in this cell line.

EXAMPLE 15

Figure 6:
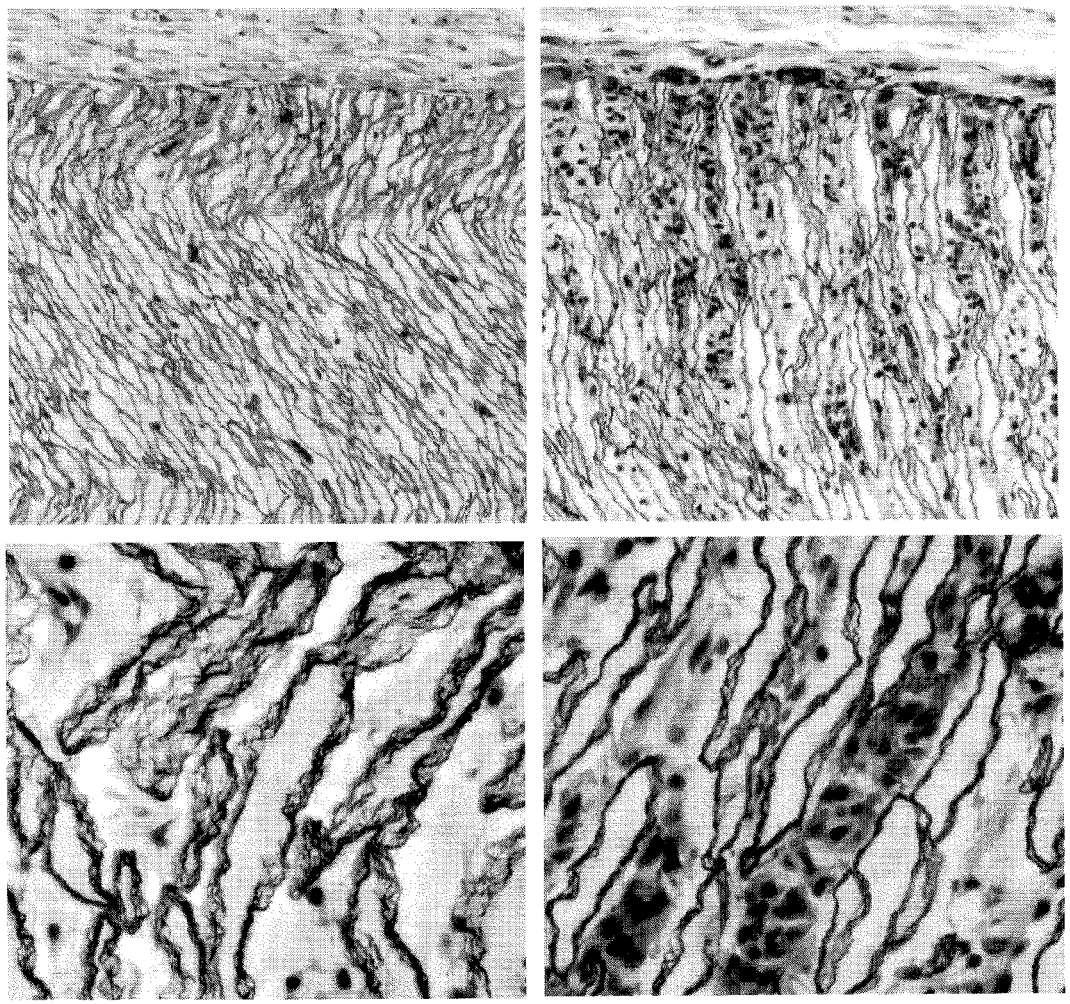
FIG. 6. Hemotoxylin and eosin staining of tissue ePTFE interface. The left panels illustrate the poor tissue penetration into uncoated ePTFE. Panels on the right illustrate a robust penetration of tissue into ePTFE coated with LA2. Original magnification: 100× (top panels) and 400× (bottom panels).
Figure 7:
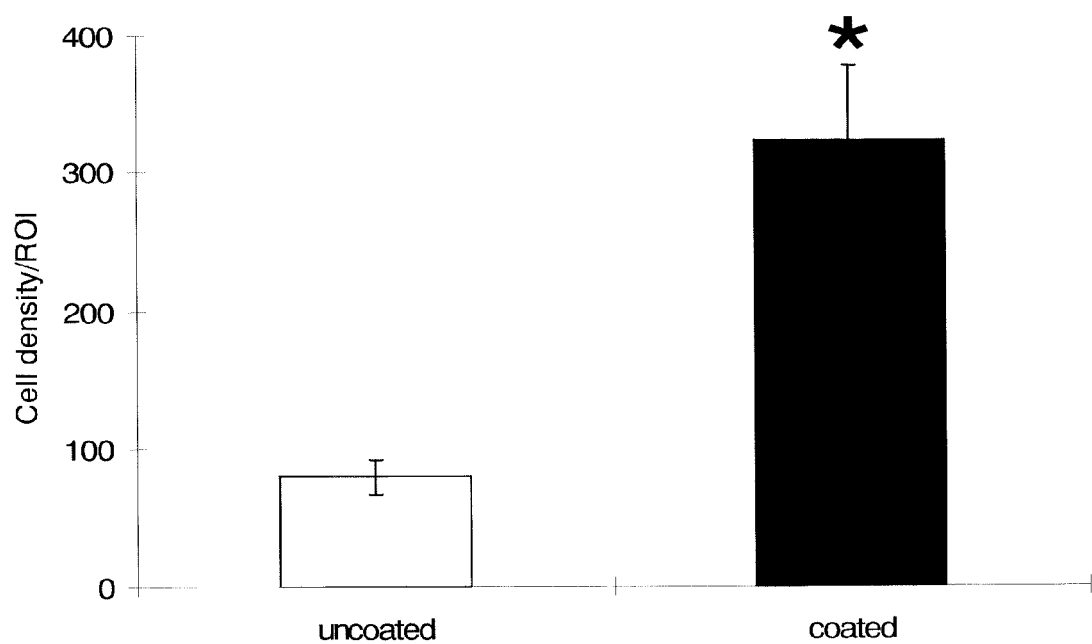
FIG. 7. Comparative cell density in ePTFE. Data is presented as the average ±S.D. The asterisk indicates p<0.001 as determined using t testing.

Collectively, the effects of LA2 as a coating on a broad range of cell types suggested LA2 would improve tissue integration and growth on implanted materials. To evaluate this hypothesis, ePTFE was used as a test substrate for LA2. ePTFE was selected as it is widely used in medical devices, the biological response to ePTFE is benign, and it does not support either effective tissue attachment or tissue integration. We hypothesized that ePTFE coated with LA2 would display improved tissue integration. Compared to uncoated ePTFE, specimens coated with LA2 exhibited a statistically significant (p=0.037; Mann-Whitney Rank Sum Test)

increase of tissue penetration into the implants (FIG. 6). In this analysis, the depth of tissue penetration was monitored by histomorphometric methods and scored on a scale of 1-4 (in 25% increments). The cell density was also statistically increased (p=<0.001, t test) towards the center of the implants as determined by counting the cell density in a specified region-of-interest (ROI) (FIG. 7). At the single time point examined, two weeks after implant, there was little evidence of inflammation in either the coated or uncoated specimens.

EXAMPLE 16

LA2 was evaluated in vivo for its ability to stimulate angiogenesis using an angiogenesis model based on the use of Matrigel implants in C57BL/6 mice, as described in Passaniti, A., Taylor, R. M., Pili, R., Guo, Y., Long, P. V., Haney, J. A., Pauly, R. R., Grant, D. S., and Martin, G. R. A simple, quantitative method for assessing angiogenesis and antiangiogenic agents using reconstituted basement membrane, heparin, and fibroblast growth factor. Lab Invest, 67: 519-528, 1992. The experiments were performed under an approved IACUC protocol in accordance with the United States Department of Agriculture, Department of Health and Human Services, and the NIH policies regarding the humane care and use of laboratory animals.

Animals were randomly assigned to each treatment group. LA2 was mixed with hydroxyapatite (50% in peptide solution). The peptide/hydroxyapatite solution was then mixed with Matrigel at a 1:9 ratio. Aliquots of 0.4 ml of Matrigel with peptide/hydroxyapatite were injected subcutaneously in mice. The final amount of peptide per injection site was 50 μg.

After 14 days the animals were euthanized and the Matrigel plugs were dissected away from the host tissue and photographed. The angiogenic response was rated on a scale of 0-3 as described by Lucidarme et al. (Lucidarme, O., Nguyen, T., Kono, Y., Corbeil, J., Choi, S. H., Varner, J., and Mattrey, R. F. Angiogenesis model for ultrasound contrast research: exploratory study. Acad Radiol, 11: 4-12, 2004). Plugs with no blood vessels were assigned a score of 0, those with few tiny peripheral vessels were assigned 1, those with larger vessels with shallow penetration scored 2, and those with several large vessels with deep penetration were scored 3.

At a two weeks time point, LA2 stimulated angiogenesis when co-injected with Matrigel. The angiogenesis score in the Matrigel with peptide/hydroxyapatite-injected mice was 3±0, while the Matrigel-only control was 0.67±0.58. This demonstrated that the laminin-derived LA2 peptide is angiogenic in this in vivo model.

The preceding examples can be repeated with similar success by substituting the generically or specifically described peptide sequences, reagents, cell lines and other conditions provided in this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A multi-domain peptide of formula I:

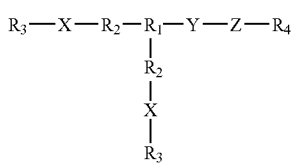

wherein:
each X is selected from SEQ ID NO 3-18 and RGD;
$R_1$ is the single trifunctional amino acid residue;
Each $R_2$ is the same or different and comprises from 0 to 5 amino acid residues covalently bonded to $R_1$ and X;

Each $R_3$ is hydrogen (H) such that the terminal group is $NH_2$, or is an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or is from one to three amino acid residues with a terminal H, such that the terminal group is $NH_2$, or an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative;

$R_4$ is OH such that the terminal group is a carboxyl, $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or $NH-R_3$;

Y is Ahx-Ahx-Ahx covalently bonded to $R_1$ and Z; and
Z is selected from SEQ ID NO 19-24.

2. The multi-domain peptide of claim 1 wherein each $R_3$ is H—, where H is hydrogen; each X is (SEQ ID NO:16); each $R_2$ is -AA-; $R_1$ is K; Y is -Ahx-Ahx-Ahx-; Z is RKRKLE-RIAR (SEQ ID NO: 20); and $R_4$ is —$NH_2$, where N is nitrogen and H is hydrogen.

3. The multi-domain peptide of claim 1 wherein $R_1$ is an L- or D-diamine amino acid residue selected from the group consisting of 2,3 diamino propionyl amino acid, 2,4 diamino butylic amino acid, lysine and ornithine.

4. The multi-domain peptide of claim 1 wherein $R_2$ is from 1 to 5 L- or D-amino acid residues selected from the group consisting of glycine, alanine, leucine and combinations of the foregoing.

5. The multi-domain peptide of claim 1 wherein the multi-domain peptide has an avidity for heparin such that the multi-domain peptide binds heparin in 0.15 M NaCl, but is eluted by greater than about 0.5 M NaCl.

6. The multi-domain peptide of claim 1 of the formula H-SIKVAVAAK(H-SIKVAVAA)-Ahx-Ahx-Ahx-RKRKLE-RIAR-$NH_2$.

* * * * *

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial
<220> FEATURE:
<223> OTHER INFORMATION: Cellular attachment peptide sequence

<400> SEQUENCE: 1

Tyr Ile Gly Ser Arg
1               5

<210> SEQ ID NO 2
<211> LENGTH: 5
<212> TYPE: PRT
<213> ORGANISM: Artificial
<220> FEATURE:
<223> OTHER INFORMATION: Cellular attachment peptide sequence

<400> SEQUENCE: 2

Ile Lys Val Ala Val
1               5

<210> SEQ ID NO 3
<211> LENGTH: 21
<212> TYPE: PRT
<213> ORGANISM: Artificial
<220> FEATURE:
<223> OTHER INFORMATION: Cellular attachment peptide sequence

<400> SEQUENCE: 3
```

-continued

```
Lys Glu Gly Tyr Lys Val Arg Leu Asp Leu Asn Ile Thr Leu Glu Phe
1               5                   10                  15

Arg Thr Thr Ser Lys
            20

<210> SEQ ID NO 4
<211> LENGTH: 17
<212> TYPE: PRT
<213> ORGANISM: Artificial
<220> FEATURE:
<223> OTHER INFORMATION: Cellular attachment peptide sequence

<400> SEQUENCE: 4

Lys Ala Thr Pro Met Leu Lys Met Arg Thr Ser Phe His Gly Cys Ile
1               5                   10                  15

Lys

<210> SEQ ID NO 5
<211> LENGTH: 5
<212> TYPE: PRT
<213> ORGANISM: Artificial
<220> FEATURE:
<223> OTHER INFORMATION: Cellular attachment peptide sequence

<400> SEQUENCE: 5

Ile Lys Leu Leu Ile
1               5

<210> SEQ ID NO 6
<211> LENGTH: 14
<212> TYPE: PRT
<213> ORGANISM: Artificial
<220> FEATURE:
<223> OTHER INFORMATION: Cellular attachment peptide sequence

<400> SEQUENCE: 6

Lys Asp Phe Leu Ser Ile Glu Leu Val Arg Gly Arg Val Lys
1               5                   10

<210> SEQ ID NO 7
<211> LENGTH: 6
<212> TYPE: PRT
<213> ORGANISM: Artificial
<220> FEATURE:
<223> OTHER INFORMATION: Cellular attachment peptide sequence

<400> SEQUENCE: 7

Leu Gly Thr Ile Pro Gly
1               5

<210> SEQ ID NO 8
<211> LENGTH: 7
<212> TYPE: PRT
<213> ORGANISM: Artificial
<220> FEATURE:
<223> OTHER INFORMATION: Cellular attachment peptide sequence

<400> SEQUENCE: 8

Arg Tyr Val Val Leu Pro Arg
1               5

<210> SEQ ID NO 9
<211> LENGTH: 5
<212> TYPE: PRT
<213> ORGANISM: Artificial
<220> FEATURE:
```

```
<223> OTHER INFORMATION: Cellular attachment peptide sequence

<400> SEQUENCE: 9

Pro Asp Ser Gly Arg
1               5

<210> SEQ ID NO 10
<211> LENGTH: 7
<212> TYPE: PRT
<213> ORGANISM: Artificial
<220> FEATURE:
<223> OTHER INFORMATION: Cellular attachment peptide sequence

<400> SEQUENCE: 10

Tyr Phe Gln Arg Tyr Leu Ile
1               5

<210> SEQ ID NO 11
<211> LENGTH: 8
<212> TYPE: PRT
<213> ORGANISM: Artificial
<220> FEATURE:
<223> OTHER INFORMATION: Cellular attachment peptide sequence

<400> SEQUENCE: 11

Leu Arg Glu Ile Lys Leu Leu Ile
1               5

<210> SEQ ID NO 12
<211> LENGTH: 10
<212> TYPE: PRT
<213> ORGANISM: Artificial
<220> FEATURE:
<223> OTHER INFORMATION: Cellular attachment peptide sequence

<400> SEQUENCE: 12

Arg Asn Ile Ala Glu Ile Ile Lys Asp Ile
1               5                   10

<210> SEQ ID NO 13
<211> LENGTH: 7
<212> TYPE: PRT
<213> ORGANISM: Artificial
<220> FEATURE:
<223> OTHER INFORMATION: Cellular attachment peptide sequence

<400> SEQUENCE: 13

Ser Ile Tyr Ile Thr Arg Phe
1               5

<210> SEQ ID NO 14
<211> LENGTH: 6
<212> TYPE: PRT
<213> ORGANISM: Artificial
<220> FEATURE:
<223> OTHER INFORMATION: Cellular attachment peptide sequence

<400> SEQUENCE: 14

Ile Ala Arg Gln Arg Asn
1               5

<210> SEQ ID NO 15
<211> LENGTH: 8
<212> TYPE: PRT
<213> ORGANISM: Artificial
<220> FEATURE:
<223> OTHER INFORMATION: Cellular attachment peptide sequence
```

```
<400> SEQUENCE: 15

Leu Gln Val Gln Leu Ser Ile Arg
1               5

<210> SEQ ID NO 16
<211> LENGTH: 6
<212> TYPE: PRT
<213> ORGANISM: Artificial
<220> FEATURE:
<223> OTHER INFORMATION: Cellular attachment peptide sequence

<400> SEQUENCE: 16

Ser Ile Lys Val Ala Val
1               5

<210> SEQ ID NO 17
<211> LENGTH: 22
<212> TYPE: PRT
<213> ORGANISM: Artificial
<220> FEATURE:
<223> OTHER INFORMATION: Cellular attachment peptide sequence

<400> SEQUENCE: 17

Lys Gln Asn Cys Leu Ser Ser Arg Ala Ser Phe Arg Gly Cys Val Arg
1               5                   10                  15

Asn Leu Arg Leu Ser Arg
            20

<210> SEQ ID NO 18
<211> LENGTH: 7
<212> TYPE: PRT
<213> ORGANISM: Artificial
<220> FEATURE:
<223> OTHER INFORMATION: Cellular attachment peptide sequence

<400> SEQUENCE: 18

Phe His Arg Arg Ile Lys Ala
1               5

<210> SEQ ID NO 19
<211> LENGTH: 9
<212> TYPE: PRT
<213> ORGANISM: Artificial
<220> FEATURE:
<223> OTHER INFORMATION: Synthetic Heparin-Binding Sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 19

Lys Arg Lys Arg Lys Arg Xaa Lys Arg
1               5

<210> SEQ ID NO 20
<211> LENGTH: 10
<212> TYPE: PRT
<213> ORGANISM: Artificial
<220> FEATURE:
<223> OTHER INFORMATION: Synthetic Heparin-Binding Sequence

<400> SEQUENCE: 20

Arg Lys Arg Lys Leu Glu Arg Ile Ala Arg
1               5                   10
```

```
<210> SEQ ID NO 21
<211> LENGTH: 10
<212> TYPE: PRT
<213> ORGANISM: Artificial
<220> FEATURE:
<223> OTHER INFORMATION: Synthetic Heparin-Binding Sequence

<400> SEQUENCE: 21

Arg Lys Arg Lys Leu Gly Arg Ile Ala Arg
1               5                   10

<210> SEQ ID NO 22
<211> LENGTH: 10
<212> TYPE: PRT
<213> ORGANISM: Artificial
<220> FEATURE:
<223> OTHER INFORMATION: Synthetic Heparin-Binding Sequence

<400> SEQUENCE: 22

Arg Lys Arg Lys Leu Trp Arg Ala Arg Ala
1               5                   10

<210> SEQ ID NO 23
<211> LENGTH: 9
<212> TYPE: PRT
<213> ORGANISM: Artificial
<220> FEATURE:
<223> OTHER INFORMATION: Synthetic Heparin-Binding Sequence

<400> SEQUENCE: 23

Arg Lys Arg Leu Asp Arg Ile Ala Arg
1               5

<210> SEQ ID NO 24
<211> LENGTH: 11
<212> TYPE: PRT
<213> ORGANISM: Artificial
<220> FEATURE:
<223> OTHER INFORMATION: Synthetic Heparin-Binding Sequence

<400> SEQUENCE: 24

Arg Lys Arg Lys Leu Glu Arg Ile Ala Arg Cys
1               5                   10

<210> SEQ ID NO 25
<211> LENGTH: 19
<212> TYPE: PRT
<213> ORGANISM: Artificial
<220> FEATURE:
<223> OTHER INFORMATION: Random sequence

<400> SEQUENCE: 25

Lys Pro Val Ser Leu Ser Tyr Arg Ala Pro Ala Arg Phe Phe Glu Ser
1               5                   10                  15

His Val Ala

<210> SEQ ID NO 26
<211> LENGTH: 15
<212> TYPE: PRT
<213> ORGANISM: Artificial
<220> FEATURE:
<223> OTHER INFORMATION: Random sequence

<400> SEQUENCE: 26

Asp Thr Ala Tyr Lys Asp Trp Pro Asn Leu Phe Arg Glu Ile Arg
1               5                   10                  15
```

```
<210> SEQ ID NO 27
<211> LENGTH: 4
<212> TYPE: PRT
<213> ORGANISM: Artificial
<220> FEATURE:
<223> OTHER INFORMATION: synthetic heparin-binding sequence
<220> FEATURE:
<221> NAME/KEY: XXXX
<222> LOCATION: (1)..(2)
<223> OTHER INFORMATION: X independently represents lysine, arginine or
      histidine
<220> FEATURE:
<221> NAME/KEY: XXXX
<222> LOCATION: (3)..(3)
<223> OTHER INFORMATION: X represent a naturally occurring or
      non-naturally occurring amino acid
<220> FEATURE:
<221> NAME/KEY: XXXX
<222> LOCATION: (4)..(4)
<223> OTHER INFORMATION: X independently represents lysine, arginine or
      histidine

<400> SEQUENCE: 27

Xaa Xaa Xaa Xaa
1

<210> SEQ ID NO 28
<211> LENGTH: 6
<212> TYPE: PRT
<213> ORGANISM: Artificial
<220> FEATURE:
<223> OTHER INFORMATION: synthetic heparin-binding sequence
<220> FEATURE:
<221> NAME/KEY: XXXXXX
<222> LOCATION: (1)..(3)
<223> OTHER INFORMATION: X independently represents lysine, arginine, or
      histidine
<220> FEATURE:
<221> NAME/KEY: XXXXXX
<222> LOCATION: (4)..(5)
<223> OTHER INFORMATION: X independently represents naturally occurring,
      or non-naturally occurring amino acid
<220> FEATURE:
<221> NAME/KEY: XXXXXX
<222> LOCATION: (6)..(6)
<223> OTHER INFORMATION: X independently represents lysine, arginine, or
      histidine

<400> SEQUENCE: 28

Xaa Xaa Xaa Xaa Xaa Xaa
1               5
```